(12) United States Patent
Davis et al.

(10) Patent No.: US 10,092,416 B2
(45) Date of Patent: Oct. 9, 2018

(54) INTERVERTEBRAL DEVICES AND RELATED METHODS

(71) Applicant: Spine View, Inc., San Jose, CA (US)

(72) Inventors: John Davis, Sunnyvale, CA (US); Al Mirel, Redwood City, CA (US); Mark Dias, San Jose, CA (US)

(73) Assignee: Expanding Innovations, Inc., Mountain View, CA (US)

( * ) Notice: Subject to any disclaimer, the term of this patent is extended or adjusted under 35 U.S.C. 154(b) by 0 days.

(21) Appl. No.: 14/120,375

(22) Filed: May 14, 2014

(65) Prior Publication Data

US 2014/0343677 A1    Nov. 20, 2014

Related U.S. Application Data

(60) Provisional application No. 61/822,919, filed on May 14, 2013, provisional application No. 61/857,252, filed on Jul. 23, 2013, provisional application No. 61/955,757, filed on Mar. 19, 2014.

(51) Int. Cl.
  *A61F 2/44*     (2006.01)
  *A61F 2/46*     (2006.01)
  *A61F 2/30*     (2006.01)

(52) U.S. Cl.
  CPC .......... *A61F 2/447* (2013.01); *A61F 2/4611* (2013.01); *A61F 2002/3055* (2013.01); *A61F 2002/3093* (2013.01); *A61F 2002/30507* (2013.01); *A61F 2002/30537* (2013.01); *A61F 2002/30538* (2013.01); *A61F 2002/30556* (2013.01); *A61F 2002/30579* (2013.01); *A61F 2002/30772* (2013.01); *A61F 2002/4628* (2013.01)

(58) Field of Classification Search
  CPC ............ A61F 2/447; A61F 2002/30515; A61F 2002/30387; A61F 2002/30556
  See application file for complete search history.

(56) References Cited

U.S. PATENT DOCUMENTS

| 5,860,973 | A   |   | 1/1999  | Michelson              |
|-----------|-----|---|---------|------------------------|
| 5,865,848 | A   | * | 2/1999  | Baker ........... A61F 2/4455 606/247 |
| 6,562,074 | B2  |   | 5/2003  | Gerbec et al.          |
| 6,648,917 | B2  |   | 11/2003 | Gerbec et al.          |
| 6,852,129 | B2  |   | 2/2005  | Gerbec et al.          |
| 6,863,673 | B2  |   | 3/2005  | Gerbec et al.          |

(Continued)

FOREIGN PATENT DOCUMENTS

WO    WO 2013/036707    3/2013

*Primary Examiner* — Jacqueline Johanas
(74) *Attorney, Agent, or Firm* — Ross M. Carothers

(57) ABSTRACT

Intervertebral devices and systems, and methods of their use, are disclosed having configurations suitable for placement between two adjacent vertebrae, replacing the functionality of the disc therebetween. Intervertebral devices and systems contemplated herein are implantable devices intended for replacement of a vertebral disc, which may have deteriorated due to disease for example. The intervertebral devices and systems are configured to allow for ample placement of therapeutic agents therein, including bone growth enhancement material, which may lead to better fusion between adjacent vertebral bones. The intervertebral devices and systems are configured for use in minimally invasive procedures, if desired.

16 Claims, 22 Drawing Sheets

(56) References Cited

U.S. PATENT DOCUMENTS

| | | |
|---|---|---|
| 6,986,772 B2 | 1/2006 | Michelson |
| 7,118,579 B2 | 10/2006 | Michelson |
| 7,204,853 B2 | 4/2007 | Gordon et al. |
| 7,235,082 B2 | 6/2007 | Bartish et al. |
| 7,316,714 B2 | 1/2008 | Gordon et al. |
| 7,655,027 B2 | 2/2010 | Michelson |
| 7,753,958 B2 | 7/2010 | Gordon et al. |
| 7,828,849 B2 | 11/2010 | Lim |
| 7,850,733 B2 | 12/2010 | Baynham |
| 7,909,869 B2 | 3/2011 | Gordon |
| 7,922,729 B2 | 4/2011 | Michelson |
| 7,967,867 B2 | 6/2011 | Barreiro et al. |
| 8,062,375 B2 | 11/2011 | Glerum et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,257,440 B2 | 9/2012 | Gordon et al. |
| 8,308,805 B2 | 11/2012 | Lynn et al. |
| 8,328,818 B1 | 12/2012 | Seifert et al. |
| 8,343,224 B2 | 1/2013 | Lynn et al. |
| 8,382,842 B2* | 2/2013 | Greenhalgh ........ A61B 17/8858 623/17.11 |
| 8,398,713 B2 | 3/2013 | Weiman |
| 8,435,298 B2 | 5/2013 | Weiman |
| 8,444,692 B2 | 5/2013 | Michelson |
| 8,491,659 B2 | 7/2013 | Weiman |
| 8,496,664 B2 | 7/2013 | Michelson |
| 8,518,120 B2 | 8/2013 | Glerum et al. |
| 8,556,979 B2 | 10/2013 | Glerum et al. |
| 8,585,761 B2* | 11/2013 | Theofilos ................ A61F 2/44 623/17.11 |
| 8,603,168 B2 | 12/2013 | Gordon et al. |
| 8,632,595 B2 | 1/2014 | Weiman |
| 8,647,386 B2 | 2/2014 | Gordon et al. |
| 8,679,183 B2 | 3/2014 | Glerum et al. |
| 8,685,098 B2 | 4/2014 | Glerum et al. |
| 8,696,751 B2* | 4/2014 | Ashley ................. A61F 2/442 623/17.16 |
| 8,709,086 B2 | 4/2014 | Glerum |
| 8,753,398 B2 | 6/2014 | Gordon et al. |
| 8,771,321 B2 | 7/2014 | Michelson |
| 8,828,019 B1* | 9/2014 | Raymond ............. A61F 2/4611 606/105 |
| 8,900,312 B2* | 12/2014 | McLean ................. A61F 2/442 623/17.16 |
| 9,114,026 B1* | 8/2015 | McLean ................ A61F 2/4455 |
| 9,233,007 B2* | 1/2016 | Sungarian ............... A61F 2/442 |
| 2003/0074064 A1* | 4/2003 | Gerbec ................ A61F 2/4455 623/16.11 |
| 2004/0054412 A1* | 3/2004 | Gerbec ................ A61F 2/4455 623/17.15 |
| 2004/0087947 A1* | 5/2004 | Lim ..................... A61F 2/4465 606/247 |
| 2004/0153065 A1* | 8/2004 | Lim ........................ A61F 2/442 606/53 |
| 2008/0140207 A1* | 6/2008 | Olmos .................. A61F 2/4455 623/17.16 |
| 2008/0300598 A1* | 12/2008 | Barreiro ................ A61F 2/4611 606/63 |
| 2010/0049324 A1* | 2/2010 | Valdevit .................. A61F 2/447 623/17.16 |
| 2010/0082109 A1* | 4/2010 | Greenhalgh ............ A61F 2/447 623/17.15 |
| 2010/0292796 A1* | 11/2010 | Greenhalgh ........ A61B 17/8858 623/17.11 |
| 2011/0130835 A1* | 6/2011 | Ashley ..................... A61F 2/441 623/17.11 |
| 2011/0144755 A1* | 6/2011 | Baynham ................ A61F 2/447 623/17.16 |
| 2011/0184522 A1* | 7/2011 | Melkent ................ A61F 2/4611 623/17.16 |
| 2011/0213465 A1* | 9/2011 | Landry ................... A61F 2/447 623/17.16 |
| 2011/0282453 A1* | 11/2011 | Greenhalgh ........ A61B 17/8858 623/17.16 |
| 2012/0029636 A1* | 2/2012 | Ragab .................... A61F 2/4425 623/17.11 |
| 2012/0059475 A1* | 3/2012 | Weiman ..................... A61F 2/44 623/17.16 |
| 2012/0109317 A1* | 5/2012 | Landry ................... A61F 2/447 623/17.16 |
| 2012/0150304 A1 | 6/2012 | Glerum |
| 2012/0150305 A1 | 6/2012 | Glerum |
| 2012/0158141 A1* | 6/2012 | Johnson ................ A61B 17/025 623/17.11 |
| 2012/0158146 A1 | 6/2012 | Glerum |
| 2012/0158147 A1 | 6/2012 | Glerum et al. |
| 2012/0158148 A1 | 6/2012 | Glerum |
| 2012/0226357 A1* | 9/2012 | Varela ..................... A61F 2/447 623/17.16 |
| 2013/0158663 A1* | 6/2013 | Miller ................... A61F 2/4425 623/17.16 |
| 2013/0158664 A1* | 6/2013 | Palmatier ................ A61F 2/447 623/17.16 |
| 2014/0039622 A1 | 2/2014 | Glerum et al. |
| 2014/0052254 A1 | 2/2014 | Glerum et al. |
| 2014/0058516 A1 | 2/2014 | Glerum et al. |
| 2014/0058519 A1 | 2/2014 | Glerum et al. |
| 2014/0094916 A1* | 4/2014 | Glerum ................... A61F 2/442 623/17.15 |
| 2014/0121774 A1 | 5/2014 | Glerum et al. |
| 2014/0128977 A1* | 5/2014 | Glerum ................ A61F 2/4455 623/17.16 |
| 2014/0249630 A1* | 9/2014 | Weiman ................. A61F 2/442 623/17.16 |
| 2014/0257484 A1* | 9/2014 | Flower ................... A61F 2/447 623/17.15 |
| 2014/0277487 A1* | 9/2014 | Davenport ............ A61F 2/4455 623/17.16 |
| 2014/0277488 A1* | 9/2014 | Davenport ............ A61F 2/442 623/17.16 |
| 2014/0277489 A1* | 9/2014 | Davenport ............ A61F 2/4455 623/17.16 |
| 2014/0343677 A1* | 11/2014 | Davis ..................... A61F 2/447 623/17.15 |
| 2015/0112437 A1* | 4/2015 | Davis ..................... A61F 2/447 623/17.15 |

* cited by examiner

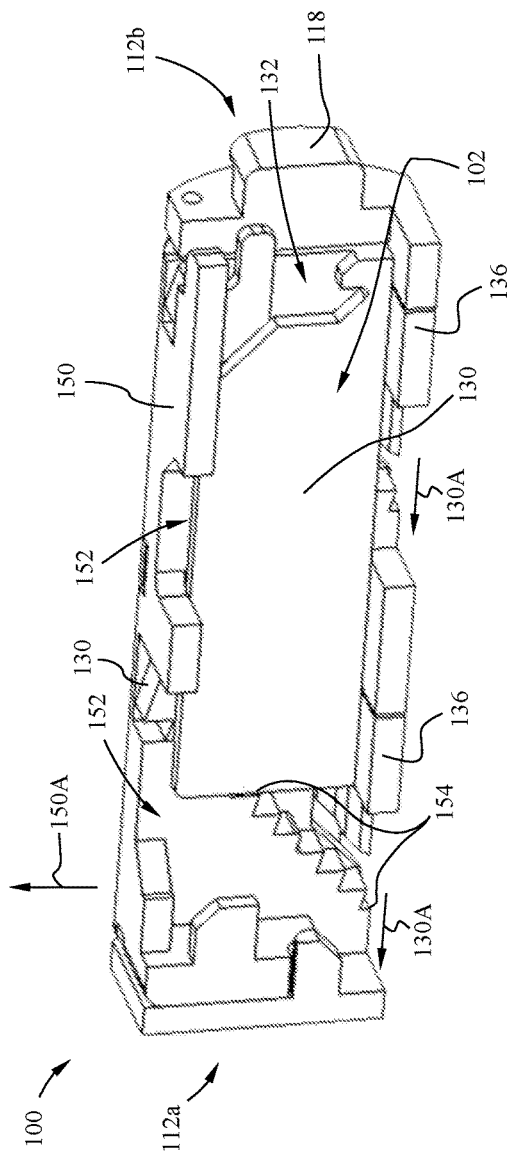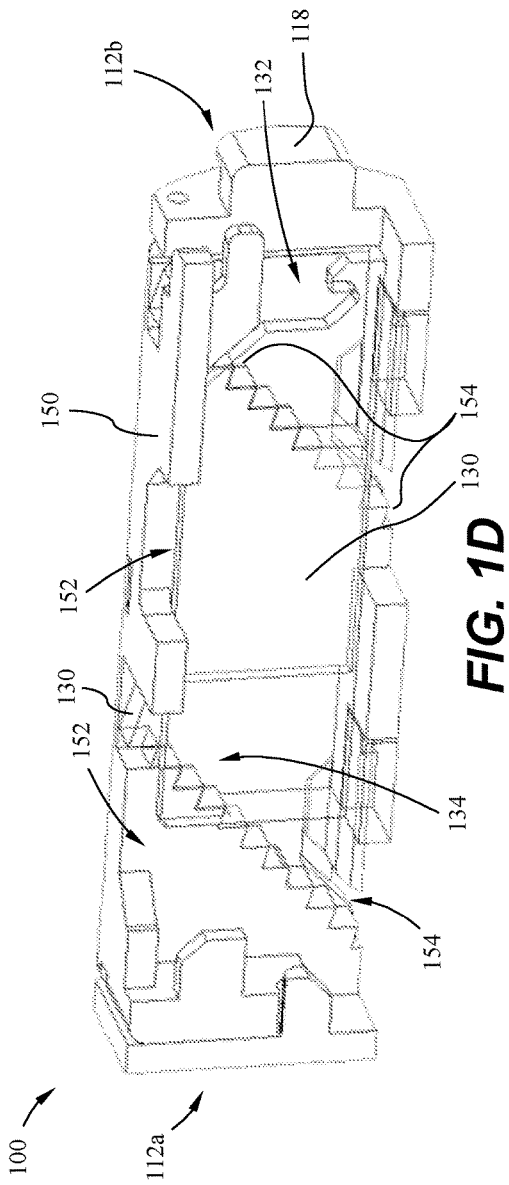

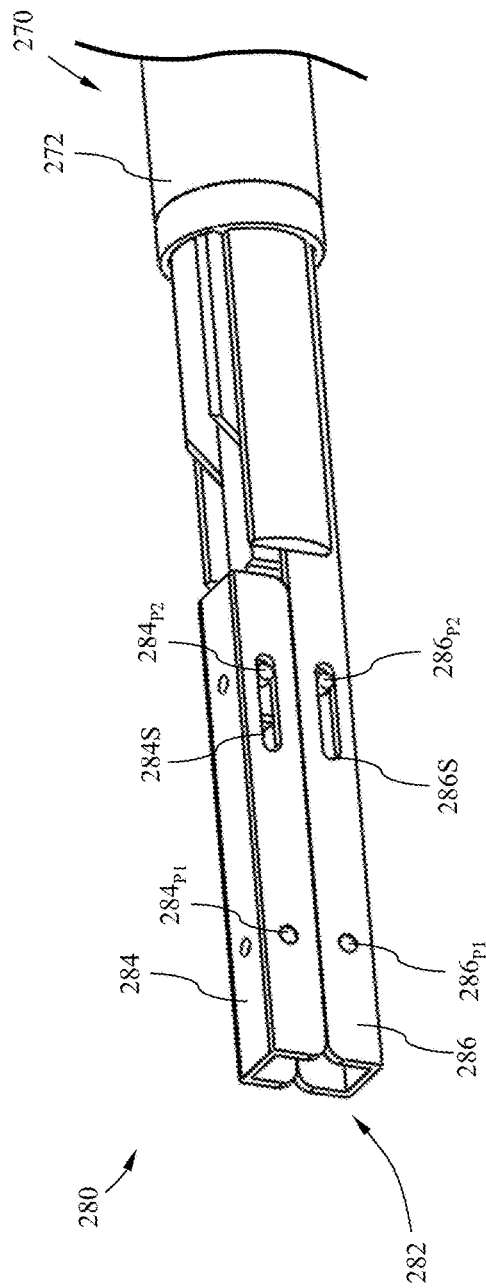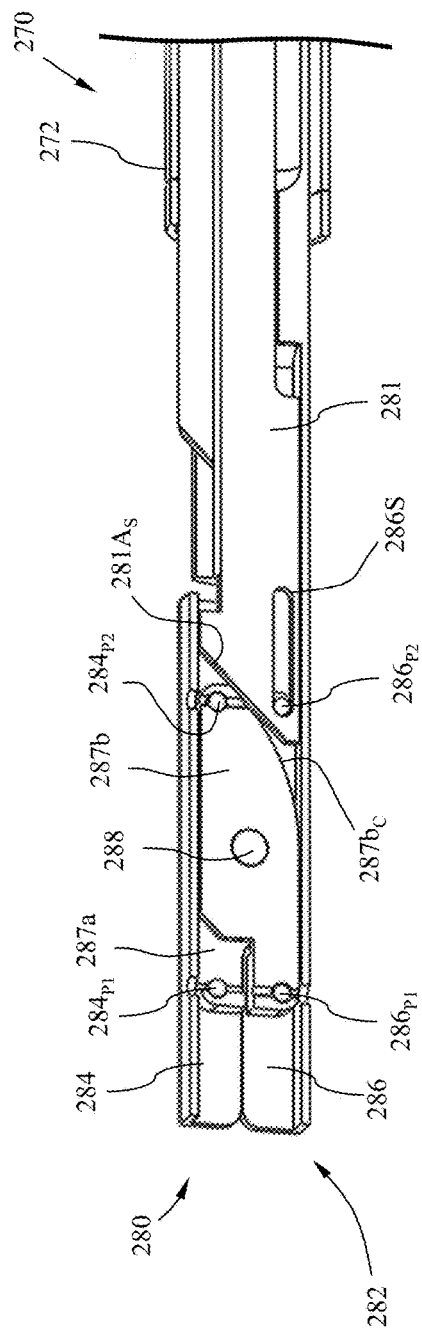

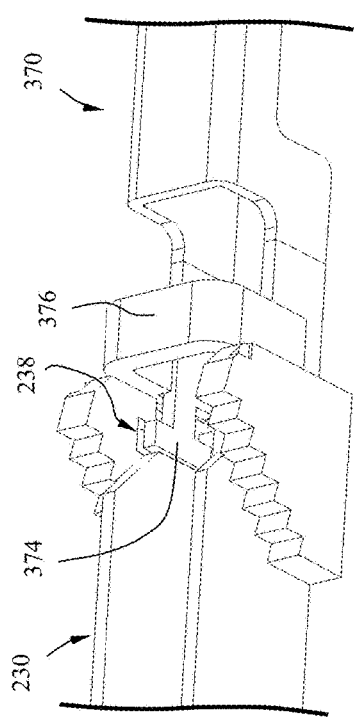
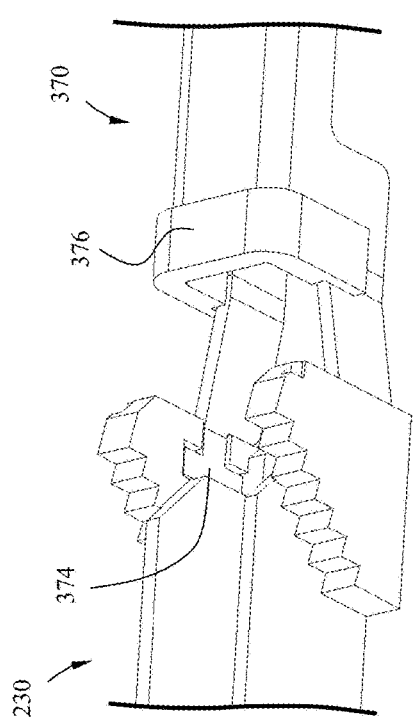
FIG. 4C
FIG. 4D

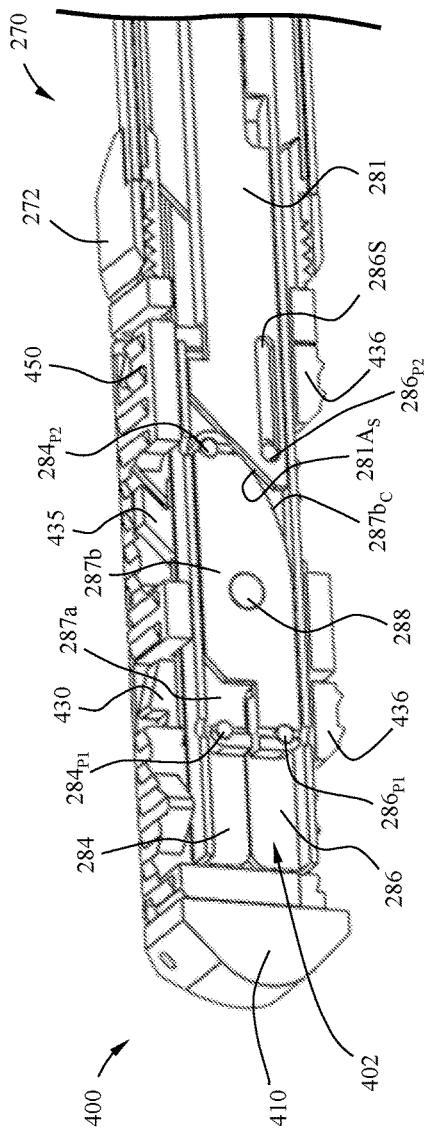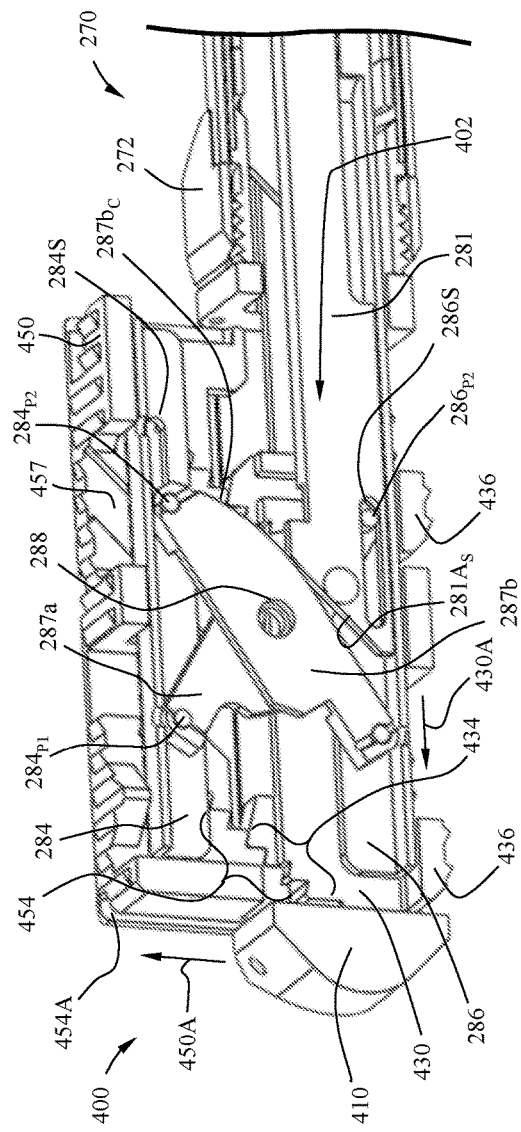

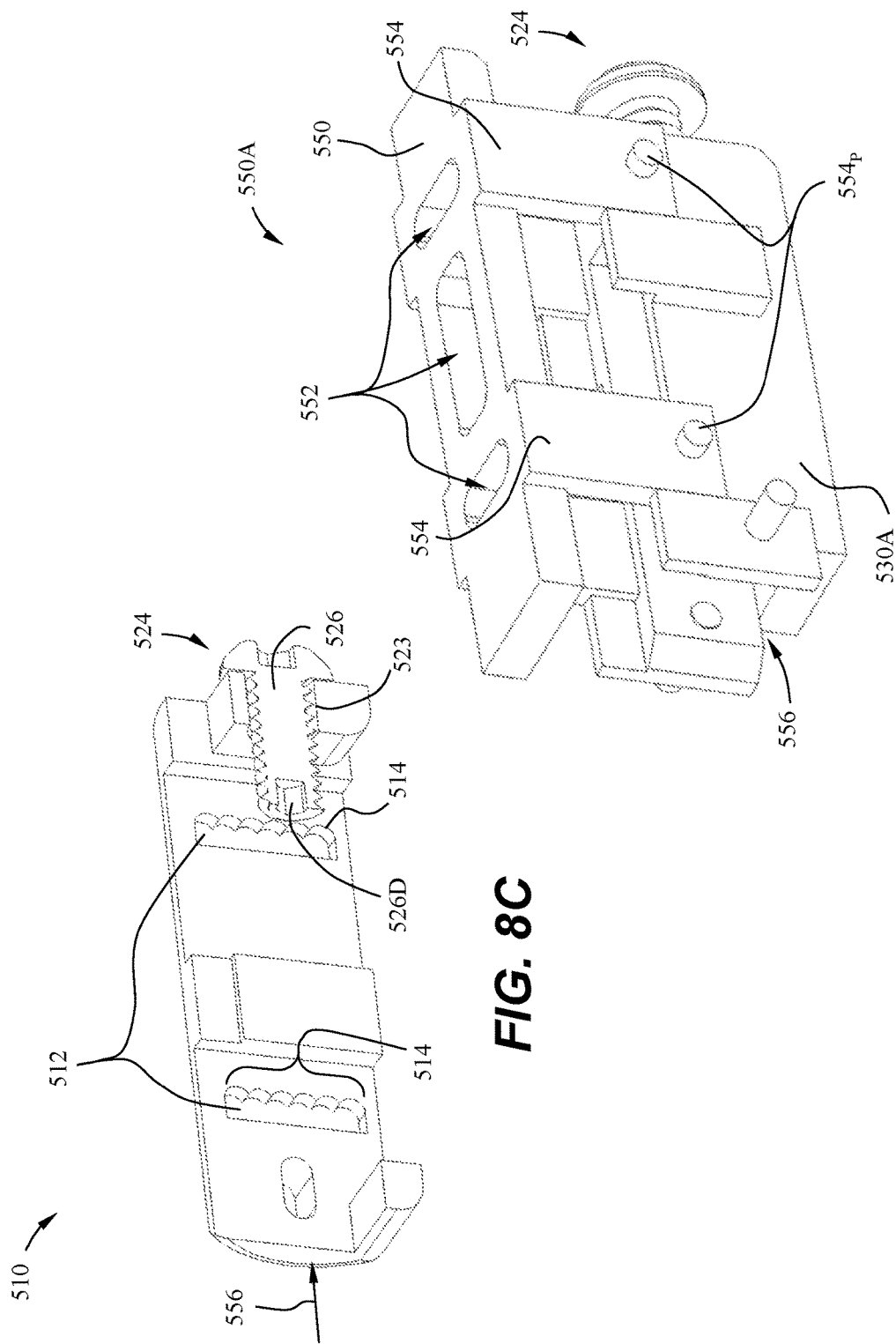

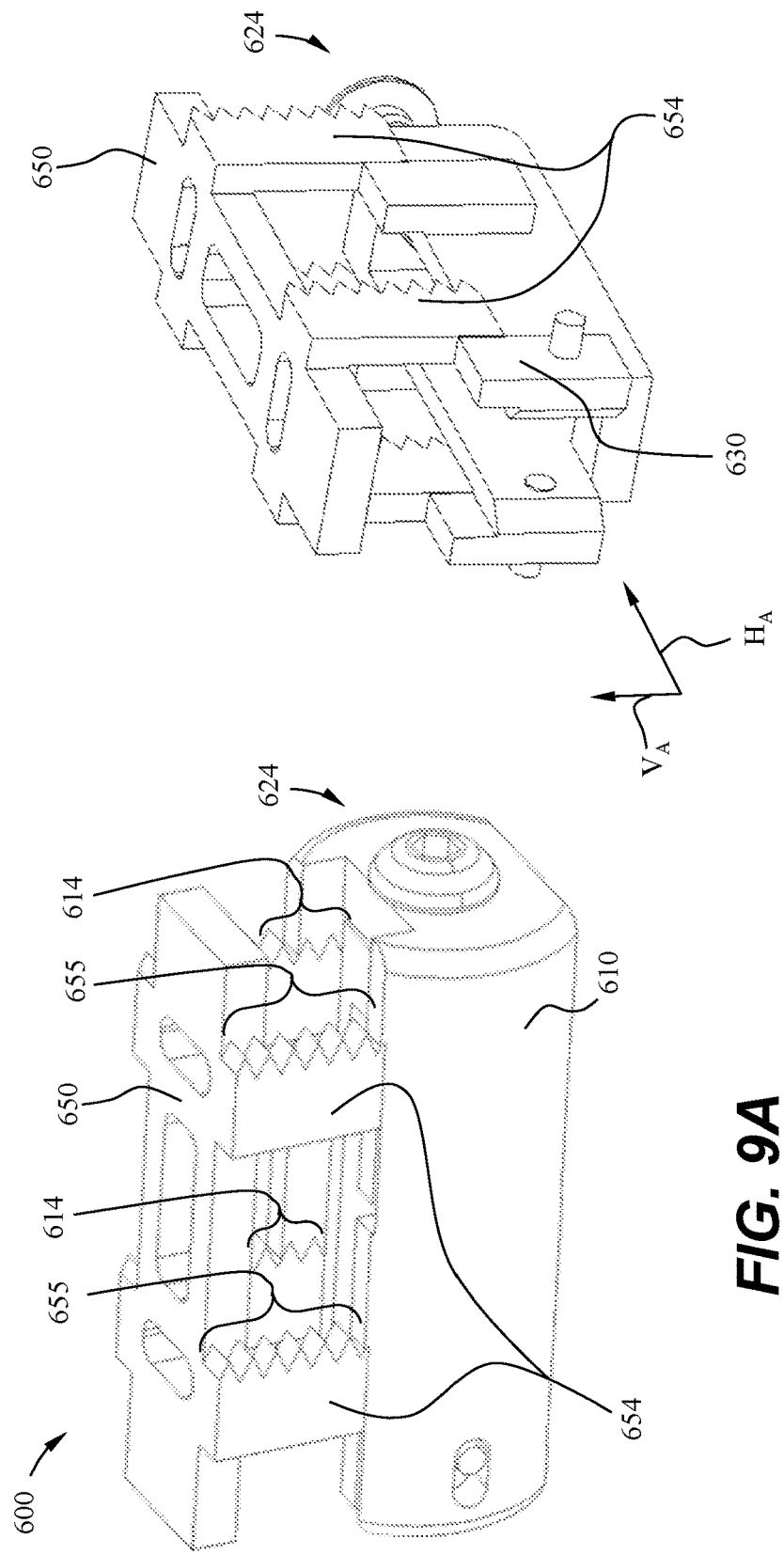

INTERVERTEBRAL DEVICES AND RELATED METHODS

This application claims priority to U.S. Provisional Application Ser. No. 61/822,919, entitled "Intervertebral Devices and Related Methods," filed May 14, 2013, U.S. Provisional Application Ser. No. 61/857,252, entitled "Intervertebral Devices and Related Methods, Filed Jul. 23, 2013, and U.S. Provisional Application Ser. No. 61/955,757, entitled "Intervertebral Devices and Related Methods," filed Mar. 19, 2014, which applications are incorporated herein by reference in their entirety.

BACKGROUND

Field of this Disclosure

This disclosure relates generally to medical devices, and more particularly, to medical devices utilized for spinal procedures.

Description of the Related Art

Degenerative disc diseases are common disorders that can impact all or a portion of a vertebral disc, a cushion-like structure located between the vertebral bodies of the spine. Degenerative disc diseases may lead, for example, to a disc herniation where the vertebral disc bulges out or extrudes beyond the usual margins of the disc and the spine. Disc herniation, in particular, is believed to be the result of excessive loading on the disc in combination with weakening of the annulus due to such factors as aging and genetics. Such degenerative disc diseases are also associated with spinal stenosis, a narrowing of the bony and ligamentous structures of the spine. Although disc herniation can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine and fecal incontinence and other neurological symptoms that can substantially impact basic daily activities and quality of life.

Temporary relief of the pain associated with disc herniation, or other degenerative disc diseases, is often sought through conservative therapy, which includes positional therapy (e.g. sitting or bending forward to reduce pressure on the spine), physical therapy, and drug therapy to reduce pain and inflammation. When conservative therapy fails to resolve a patient's symptoms, surgery may be considered to treat the structural source of the symptoms. When surgery fails to resolve a patient's symptoms, more drastic measures may include disc replacement surgery or vertebral fusion.

There are numerous implantable devices that have been developed for disc replacement and vertebral fusion. Such implantable devices, also referred to as cage systems, may be deployed to replace the vertebral disc and fuse the adjacent vertebrae, relieving pain and providing increased mobility to the patient. However, known implantable devices and methodologies have drawbacks. For example, many of the implantable devices currently available do not allow for an ample amount of materials to encourage bone growth to be positioned within and around the devices and adjacent vertebral bones. Such gone growth materials allow for a higher level of fusion of the adjacent vertebrae, providing increase stabilization and minimize the likelihood of further issues in the future. Also, many implantable devices are large structures that are not easily utilized in a minimally invasive procedure. Rather, they may require surgical procedures allowing greater access, which subjects the patient to higher risks of disease and prolonged infection.

There is a need for implantable devices intended for replacement of a vertebral disc, which allow for ample placement of bone growth material that may lead to better fusion between adjacent vertebral bones. There is a further need for such implantable devices to be provided during minimally invasive procedures, reducing the risk of infection and allowing for quicker healing of the patient.

BRIEF SUMMARY

Intervertebral devices and systems, and methods of their use, are disclosed having configurations suitable for placement between two adjacent vertebrae, replacing the functionality of the disc therebetween. Intervertebral devices and systems contemplated herein are implantable devices intended for replacement of a vertebral disc, which may have deteriorated due to disease for example. The intervertebral devices and systems are configured to allow for ample placement of therapeutic agents therein, including bone growth enhancement material, which may lead to better fusion between adjacent vertebral bones. The intervertebral devices and systems are configured for use in minimally invasive procedures, if desired.

Consistent with the present disclosure, an expandable intervertebral device includes a base having a bottom surface, a first body portion and a second body portion. The first body portion may be slideably coupled to the base and configured to move in a first direction with respect to the base. The first body portion including a first engaging element. The second body portion is slideably coupled to the base and configured to move in a second direction with respect to the base, the second body portion including a top surface and a second engaging element. The first engaging element of the first body portion is configured to couple to the second engaging element of the second body portion, such that coupling of the first and second engaging elements prevents movement of the first body portion in a third direction with respect to the base when a compression force is applied between the top surface of the second body portion and the bottom surface of the base. In certain embodiments, the third direction may be substantially opposite to the first direction. In other embodiments, the second direction is different than the first direction, or the second direction is substantially perpendicular to a longitudinal axis of the base, or the first direction is substantially perpendicular to a longitudinal axis of the base.

In still other embodiments, the top surface of the second body portion may be configured to interface with a first biological tissue, and the bottom surface of the base may be configured to interface with a second biological tissue. In other embodiments, the first body portion may include a surface configured to interface with biological tissue.

In yet other embodiments, each of the first and second engaging elements may have geometric shapes, a portion of the geometric shape of the first engaging element configured to couple to a portion of the geometric shape of the second engaging element. The geometric shape of each of the first and second engaging elements may include a shape selected from a group of shapes consisting of a triangle, a circle, a rectangle, a cylinder, or a portion of any of the shapes in this group, or a combination of any shapes, or said portion thereof. In some embodiments, the geometric shape may include a tooth structure, while in other embodiments, the geometric shape of each of the first and second engaging elements is a curvilinear geometric shape.

In yet other embodiments, the first engaging element is one of a plurality of first engaging elements, at least one of the first engaging elements being configured to engage the second engaging element. In other embodiments, the second engaging element is one of a plurality of second engaging elements, at least one of the second engaging elements being configured to engage the first engaging element. In still other embodiments, the first engaging element is one of a plurality of first engaging elements and the second engaging element is one of a plurality of second engaging elements, at least one of the first engaging elements configured to engage at least one of the second engaging elements.

In other embodiments, an expandable intervertebral device includes a plurality of heights. The height may be equal to a distance extending from the top surface of the second body portion to the bottom surface of the first body portion. Alternatively, in other embodiments, the height may be equal to a distance extending from the top surface of the second body portion to a bottom surface of the base. The base may include a first end, a second end, and a longitudinal axis extending from the first end to the second end. The first body portion may be configured to be positioned at one of a plurality of positions along the longitudinal axis of the base, each of the plurality of positions corresponding to a respective one of the plurality of heights of the expandable intervertebral device.

In other aspects, a method includes providing an expandable intervertebral device having a base, a first body portion, and a second body portion, the first body portion configured to move in a first direction with respect to the base and the second body portion configured to move in at least a second direction with respect to the base, the first body portion including a first engaging element and the second body portion including a second engaging element. The second body portion may be moved in the second direction, and the first body portion may be moved in the first direction, such that the first engaging element of the first body portion couples to the second engaging element of the second body portion, the coupling of the first and second engaging elements preventing movement of the second body portion in a third direction. In some embodiments, the third direction is substantially opposite to the second direction. In other embodiments, the second direction and the first direction are different.

In still other embodiments, each of the first and second engaging elements have geometric shapes. In certain embodiments, moving the first body portion results in the coupling of a portion of the geometric shape of the first engaging element and a portion of the geometric shape of the second engaging element. In other embodiments, moving the second body portion results in the coupling of a portion of the geometric shape of the first engaging element and a portion of the geometric shape of the second engaging element. In still other embodiments, the geometric shape of each of the first and second engaging elements includes a shape selected from a group consisting of a triangle, a circle, a rectangle, and a cylinder, while in other embodiments the geometric shape of each of the first and second engaging elements includes a tooth structure. In other embodiments, the geometric shape of each of the first and second engaging elements is a curvilinear geometric shape. In yet other embodiments, the first engaging element is one of a plurality of first engaging elements, and the second engaging element is one of a plurality of second engaging elements.

It is to be understood that both the foregoing general description and the following detailed description are exemplary and explanatory only and are not restrictive of the any embodiments, as claimed. Other objects, features and advantages of the embodiments disclosed or contemplated herein will be apparent from the drawings, and from the detailed description that follows below.

BRIEF DESCRIPTION OF THE DRAWINGS

Reference will be made to embodiments of the present disclosure, examples of which may be illustrated in the accompanying figures. These figures are intended to be illustrative, not limiting. Although the subject matter of this disclosure is generally described in the context of specific embodiments, it should be understood that it is not intended to limit the scope of the invention to these particular specific embodiments. In the drawings:

FIG. 1C is a partial section view of the intervertebral device of FIG. 1.

FIG. 1D is another partial section view of the intervertebral device of FIG. 1.

FIG. 3A is a perspective view of another exemplary delivery device.

FIG. 3B is a partial section view of the exemplary delivery device of FIG. 3A.

FIG. 4C is a perspective view of the portion of the exemplary delivery device of FIG. 4A and a portion of another exemplary intervertebral device.

FIG. 4D is another perspective view of the portion of the exemplary delivery device of FIG. 4A and the portion of the exemplary intervertebral device of FIG. 4C.

FIG. 7A is a perspective view of a portion of an exemplary delivery device and a portion of the exemplary intervertebral device of FIG. 6A.

FIG. 7B is another perspective view of the portion of the exemplary delivery device of FIG. 7A and the portion of the exemplary intervertebral device of FIG. 6A.

FIG. 8A is a perspective view of another exemplary intervertebral device.

FIG. 8B is a perspective view of a portion of the exemplary intervertebral device of FIG. 8A.

FIG. 8C is a perspective view of another portion of the exemplary intervertebral device of FIG. 8A.

FIG. 8D is a perspective view of yet another portion of the exemplary intervertebral device of FIG. 8A.

FIG. 9A is a perspective view of another exemplary intervertebral device.

FIG. 9B is a perspective view of a portion of the exemplary intervertebral device of FIG. 9A.

DETAILED DESCRIPTION

Intervertebral devices and systems, and methods of their use, are disclosed having configurations suitable for placement between two adjacent vertebrae. Intervertebral devices and systems contemplated herein are intended for replacement of a vertebral disc, which may have deteriorated due to disease for example. The intervertebral devices and systems are configured to allow for ample placement of therapeutic agents therein, including bone growth enhancement material, which may lead to better fusion between adjacent vertebral bones. The intervertebral devices and systems are configured for use in minimally invasive procedures, if desired.

The following description is set forth for the purpose of explanation in order to provide an understanding of the various embodiments of the present disclosure. However, it is apparent that one skilled in the art will recognize that embodiments of the present disclosure may be incorporated into a number of different systems and devices.

The embodiments of the present disclosure may include certain aspects each of which may be present in one or more medical devices or systems thereof. Structures and devices shown below in cross-section or in block diagram are not necessarily to scale and are illustrative of exemplary embodiments. Furthermore, the illustrated exemplary embodiments disclosed or contemplated herein may include more or less structures than depicted and are not intended to be limited to the specific depicted structures. While various portions of the present disclosure may be described relative to specific structures or processes with respect to a medical device or system using specific labels, these labels are not meant to be limiting.

The expandable intervertebral devices described herein may be made from any suitable biocompatible material, including but not limited to metals, metal alloys (e.g. stainless steel) and polymers (e.g. polycarbonate), and may be formed using any appropriate process, such as screw-machining or molding (e.g. injection molding). The intervertebral devices herein may be sized for minimally invasive procedures having operating lumens at about 12 mm or less. For illustration purposes only, any expandable intervertebral device described or contemplated herein may have a height in the range from about 6 mm to about 16 mm, and a length in the range of from about 20 to about 40 mm, and a width in the range of from about 8 mm to about 16 mm. The intervertebral devices described or contemplated herein may be positioned between adjacent vertebrae through any suitable procedure, such as through a posterior lumbar interbody approach or through a transforaminal lumbar interbody approach, for example.

Reference will now be made in detail to the present exemplary embodiments, which are illustrated in the accompanying drawings.

Figure 1A:
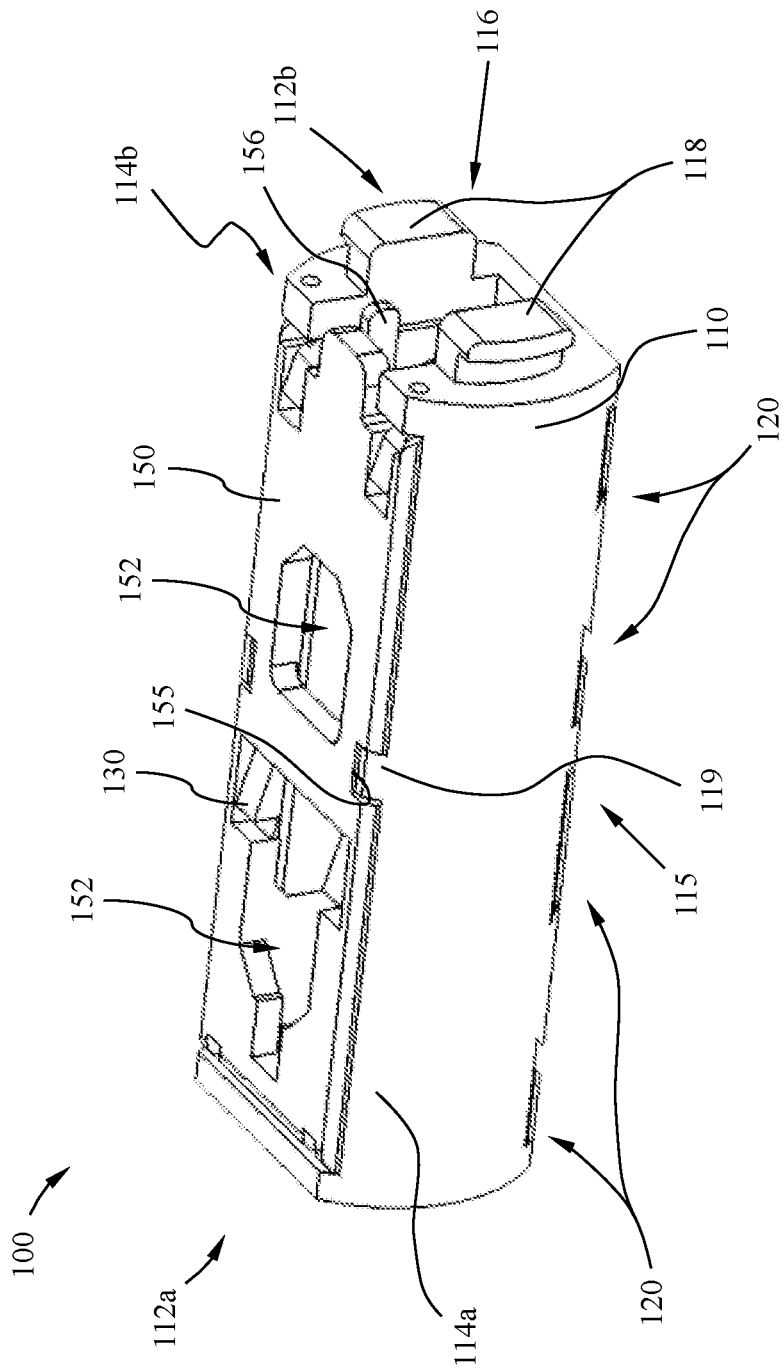
FIG. 1A is a perspective view of an intervertebral device in a first configuration.
Figure 1B:
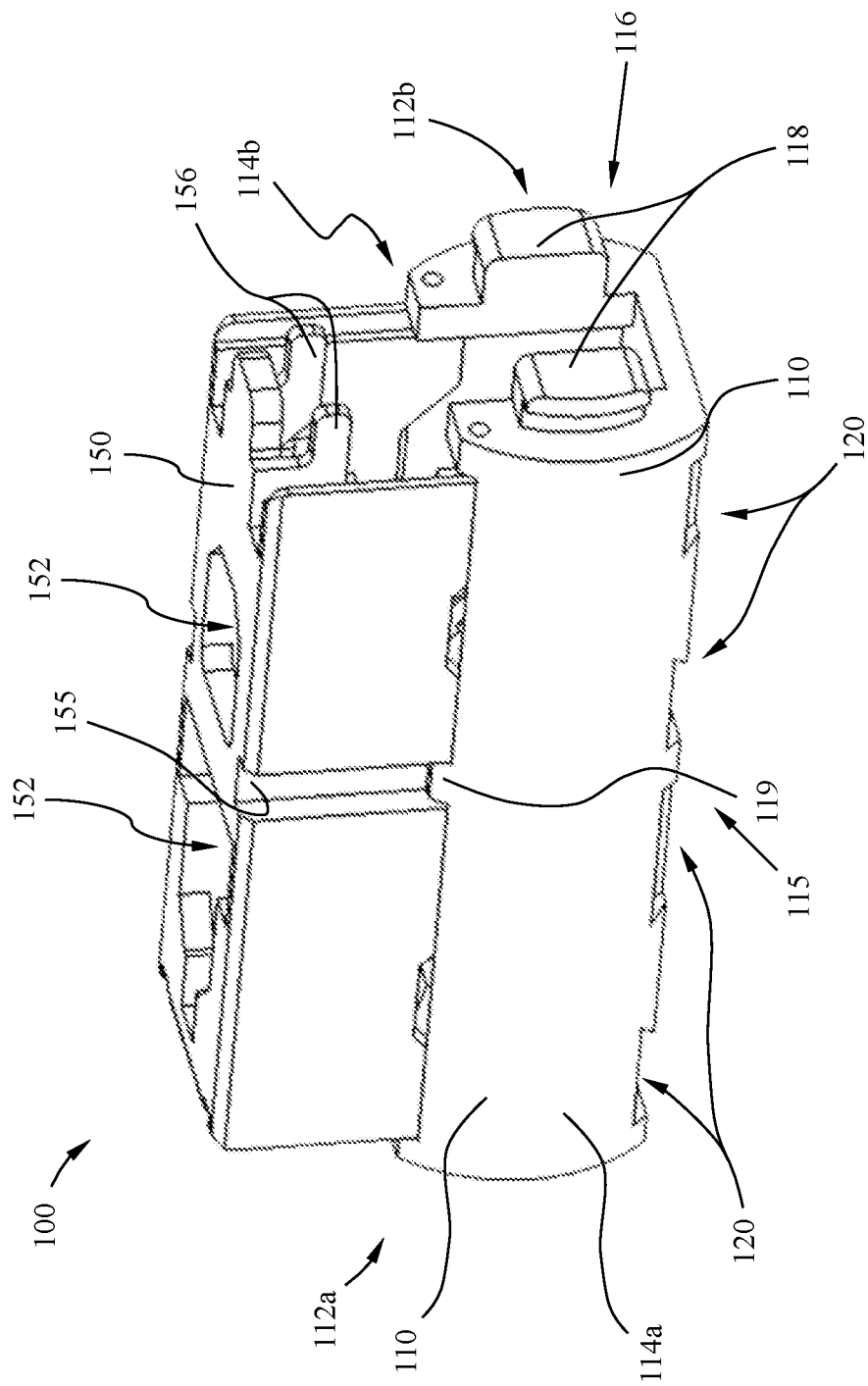
FIG. 1B is a perspective view of the intervertebral device of FIG. 1 in a second configuration.

Turning to FIGS. 1A and 1B, a perspective view of a first exemplary intervertebral device 100 includes a first element 110, a second element 130, and a third element 150. As will be better understood in the discussion below, the elements 110, 130, 150 cooperate such that the intervertebral device 100 geometric height may have a minimum, collapsed configuration, as depicted in FIG. 1A, and a maximum, expanded configuration, as depicted in FIG. 1B and discussed in greater detail below. The first element 110 may also be referred to as a base 110, the second element 130 may also be referred to as a first body portion 130, and the third element 150 may also be referred to as a second body portion 150.

The first element 110 is configured to provide a base or outer structure for the intervertebral device 100, and includes two ends or end portions 112a, 112b and two sides or side portions 114a, 114b. A bottom portion 115 includes one or more openings 120, as other elements 130, 150 may have as well, to allow for therapeutic materials, including bone growth enhancing materials to pass therethrough. One end, e.g. end 112b, may include an opening 116 for passing delivery tools utilized for expanding, contracting, or locking the intervertebral device 100. As used herein, the term "locking" used in conjunction with the intervertebral device 100, or other intervertebral device described or contemplated herein, means to substantially maintain the position of each of the elements 110, 130, 150 with respect to each other. The end 112b may also include structures 118 which allow for attachment to a delivery tool or system (not shown), as described below with respect to FIGS. 2C and 2D.

The third element 150 is slideably interfaced to the first element 110 such that the third element 150 at least slides vertically with respect to the first element 110. The third element 150 may include one or more openings 152 to allow for passage or introduction of therapeutic elements or bone growth enhancing materials therethrough. The third element 150 may also include geometric structures 156 configured to receive tools adapted to vertically move the third element 150 with respect to the first element 110. The third element 150 may also include recessed surfaces 155 adapted to receive a portion 119 of the first element 110 to limit the movement of the third element 150 to substantially one direction with respect to the first element 100. Each of the sides or sidewalls 114a, 114b of the first element 110 may be curved along its height to correspond to a delivery tube or cannula (not shown), as part of a delivery system. The sidewalls 114a, 114b may have other geometric cross-sections to correspond to elements of alternative delivery systems. The second element 130 may be positioned at least partially within the third element 150.

Turning to FIG. 1B, the exemplary intervertebral device 100 is depicted in an expanded configuration. As discussed above, protrusions 119 of the first element 110 may cooperate with recesses 155 to maintain the movement of the third element 150 in a substantially single direction with respect to the first element 110. The second element 130 may then be positioned to lock the position of the third element 150 with respect to the first element 110, at a desired intervertebral device 100 height, for deployment between two adjacent vertebrae for example.

As is better depicted in the cross-section view of intervertebral device 100 of FIG. 1C, the third element 150 may include a number of engaging elements 154 which are adapted to engage corresponding engaging elements 134 of the second element 130. Also, the second element 130 may include tabs 136 which may be adapted to slide upon tissue, for example bone tissue, in a direction defined by arrow 130A for example. The second element 130 may also include a geometric structure 132 adapted to interface to a tool (not shown) that moves the second element 130 in the direction of arrow 130A at certain times and in a direction opposite to arrow 130A at other times, as part of an insertion or delivery tool for example. Turing also to FIG. 1D, the second element 130 is depicted opaque to allow for better viewing of the engaging members 134, 154 of the second and third elements 130, 150, respectively. While depicted as engaging teeth, the engaging members 134, 154 may take on any suitable geometric configuration that allows for maintaining the position of the third member 150 with respect to the first member 110. For example, the engaging members 154 may be semicircular recesses and the engaging member 134 may be corresponding semicircular tabs adapted to engage the semicircular recesses.

Figure 1E:
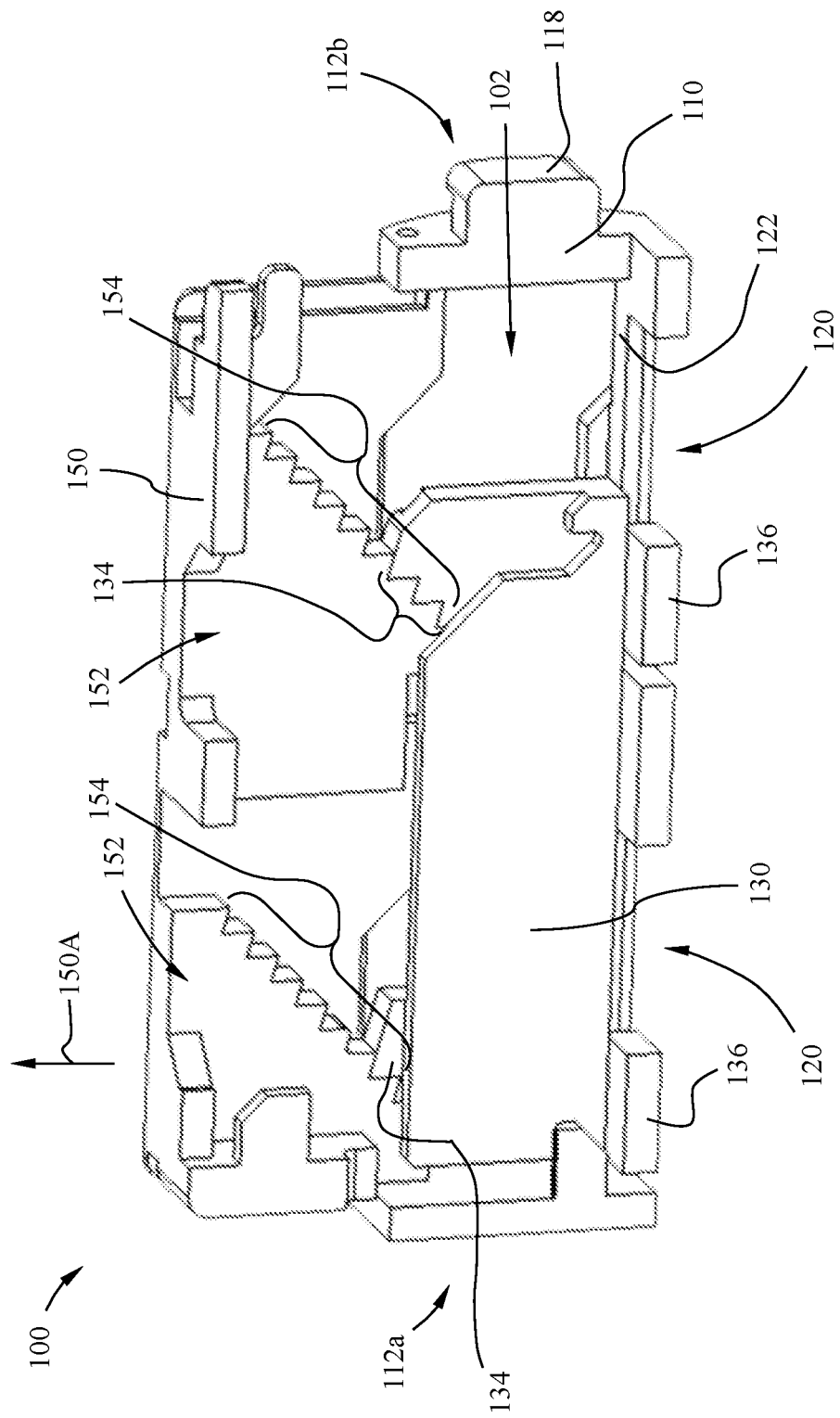
FIG. 1E is a partial section view of the intervertebral device of FIG. 1B.

In operation, with reference also to FIG. 1E, an expanding tool (not shown) may be positioned within an internal space 102 of the intervertebral device 100. The expanding tool may be configured to engage both the first element 110 and the third element 150 such that when the expanding tool is expanded the third element 150 moves substantially vertical with respect to the first element 110, as generally indicated by arrow 150A. Once the device 100 has been expanded, the expanding tool, or another tool (not shown), may be utilized to then translate or move the second element 130 in the direction of arrow 130A, as desired, the engaging members 154, 134 engaged to maintain the position of the third element 150 with respect to the first element 110 and/or the second element 130. It should be noted that the second element 130 may be configured to be slideably supported by the first element 110, upon a surface 122 of the first element 110 for example, or slideably supported by the inner wall surface of the sidewalls 114, to maintain the correct relationship of the first, second, and third elements 110, 130, 150 with respect to each other during operation. Accordingly, when positioned between two adjacent vertebrae during use, compressive forces may pass from the third element 150 to the second element 130; from the third element 150 to the first element 110; or from the third element 150 to both the first and second elements 110, 130, a first portion of the compressive force supported by the first element 110 and a second portion of the compressive force supported by the second element 130.

Figure 2A:
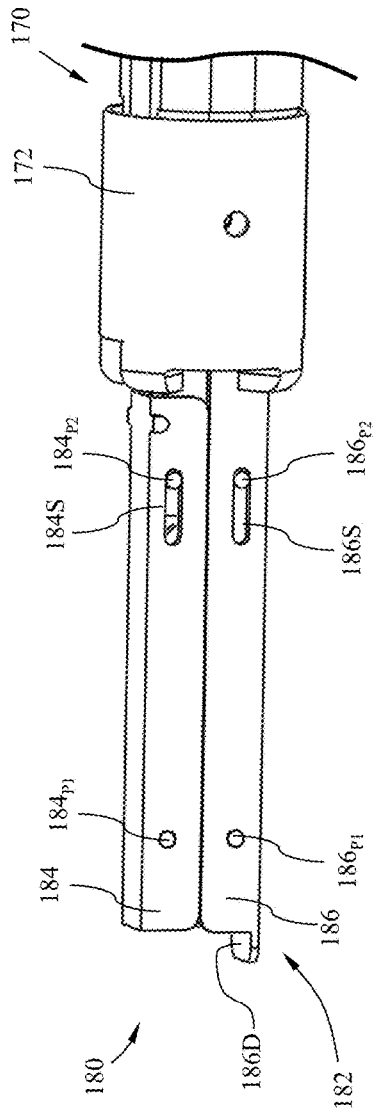
FIG. 2A is a perspective view of an exemplary deliver device in a first configuration.
Figure 2B:
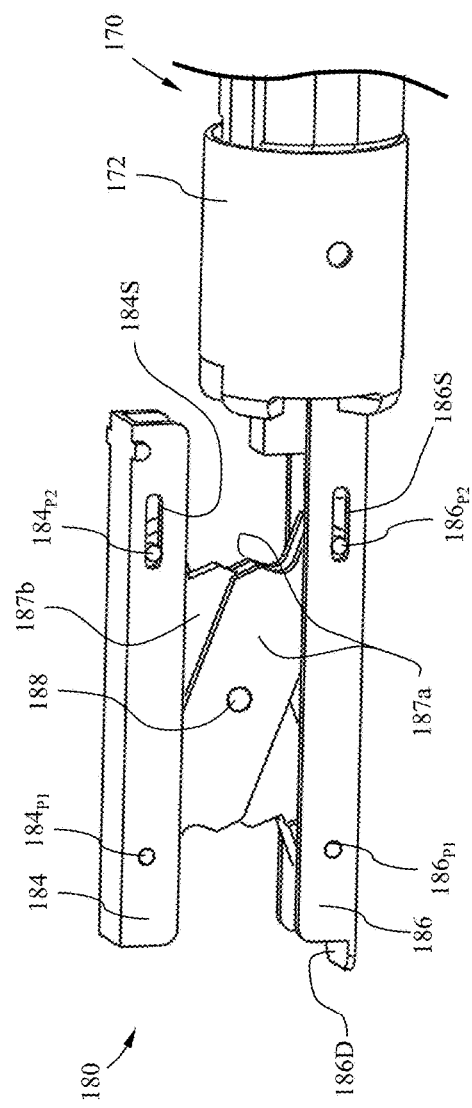
FIG. 2B is a perspective view of an exemplary deliver device in a second configuration.

Turning to FIGS. 2A and 2B, a first delivery system 170 includes an expandable device 180. Delivery system 170 includes a tubular member 172 that is configured to engage or otherwise couple to an intervertebral device, such as device 100 for example. Expandable device 180 includes an expandable distal portion 182. The expandable distal portion 182 including a first arm 184, a second arm 186, a pair of members 187a and a member 187b. Members 187a and arm 186 are rotatably coupled through a hinge 188. A distal end of each of the members 187a is rotatably coupled to the arm 184 with a pin $184_{P1}$ and a proximal end of each of the members 187a slideably attached to arm 186 through the cooperation of a pin $186_{P2}$ and corresponding slot 186S. Similarly, a distal end of the member 187b is rotatably coupled to the arm 186 with a pin $186_{P1}$ and a proximal end of the member 187b is slideably coupled to the arm 184 through the cooperation of a pin $184_{P2}$ and corresponding slot 184S. The distal end of the arm 186 may include a tab 186D that may be configured to engage an intervertebral device, such as device 100, during deployment of the device 100.

Figure 2C:
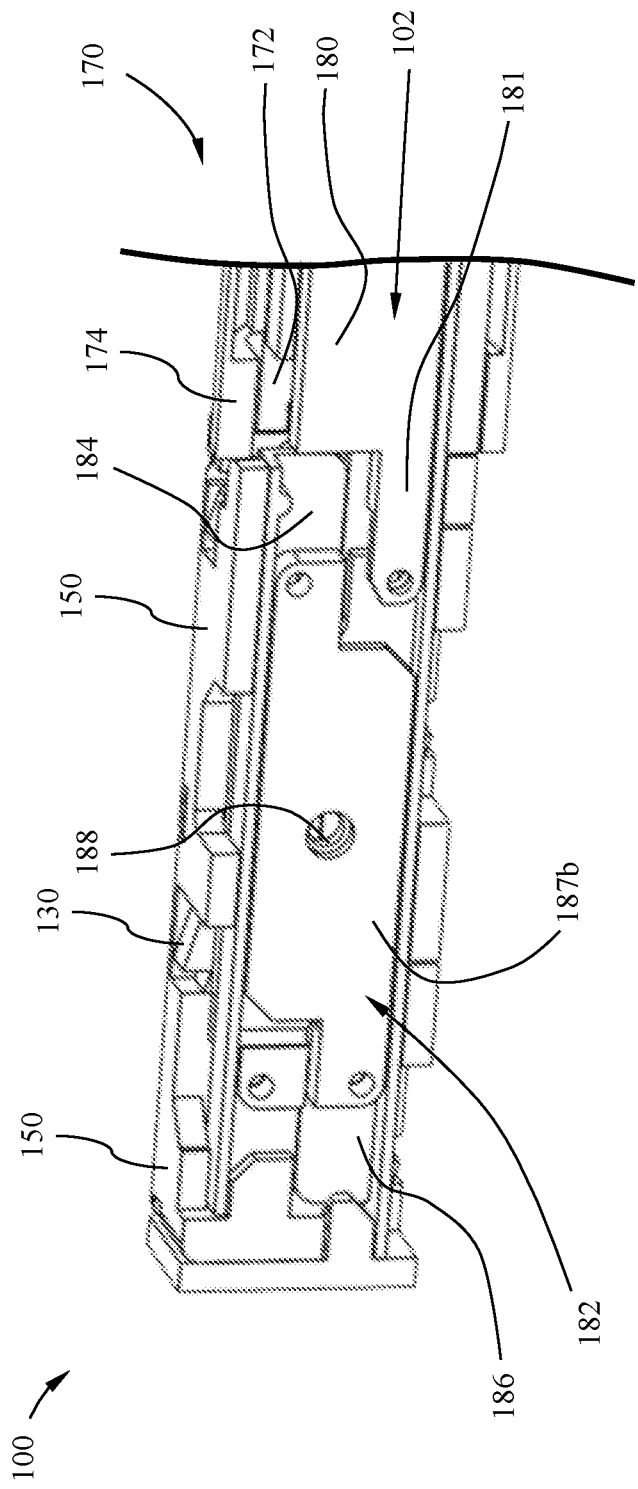
FIG. 2C is a partial section view of the intervertebral device of FIG. 1, including the exemplary delivery device of FIG. 2A.
Figure 2D:
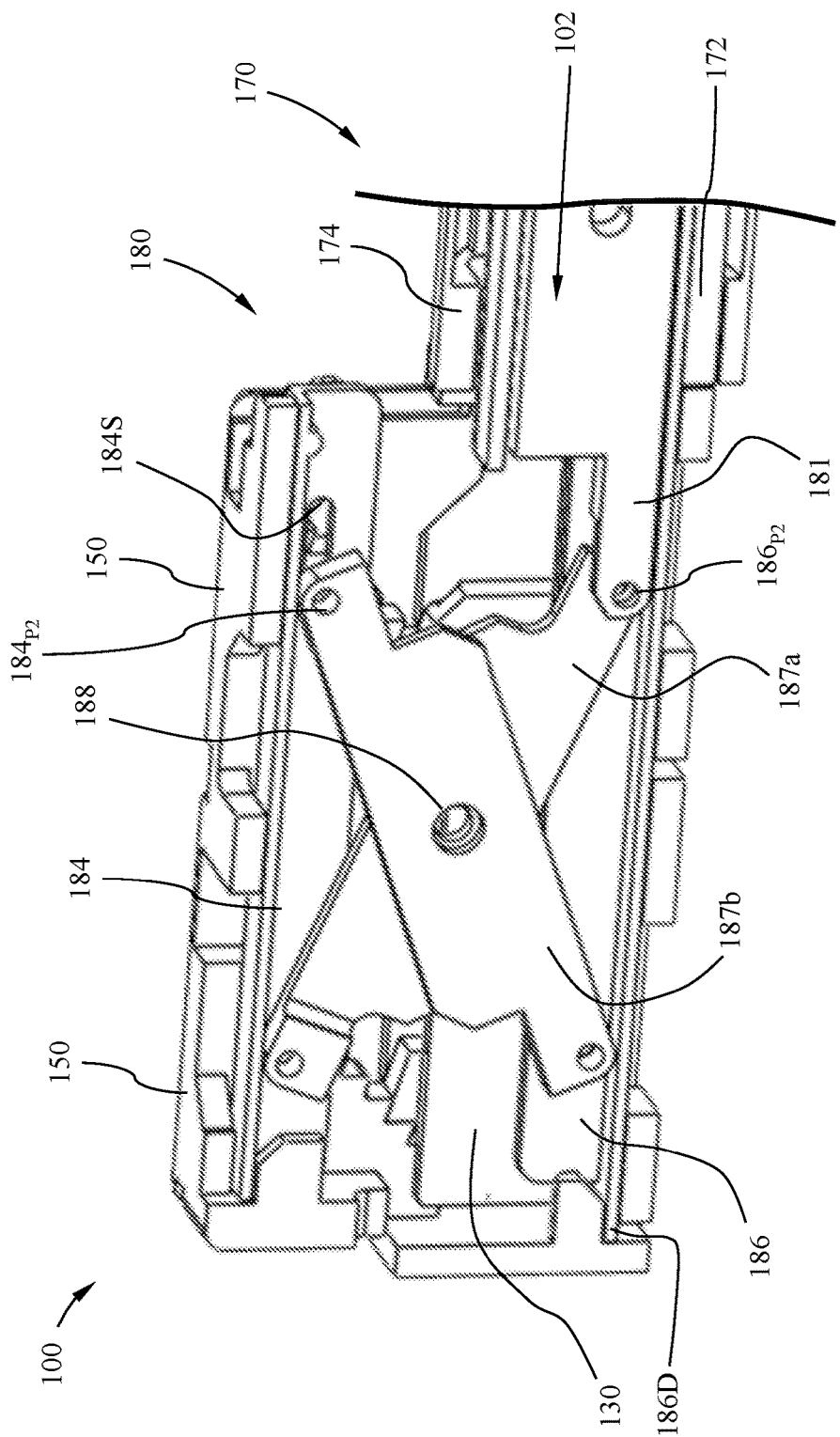
FIG. 2D is a partial section view of the intervertebral device of FIG. 2, including the exemplary deliver device of FIG. 2C.

Turning also to FIGS. 2C and 2D, the first exemplary delivery system 170 (shown in cross-section) also includes an attachment member 174 adapted to selectably grab and release the intervertebral device 100, via tabs 118 for example, and the exemplary expandable tool 180 (also shown in cross-section, e.g. not depicting a first of the pair of members 187a). The expandable device 180 may be positioned during insertion of the intervertebral device 100 into a space between two vertebrae, or may be positioned independently after the device 100 has been inserted by delivery system 170, or another insertion tool or delivery system. Alternatively, the delivery system 170 may insert the expandable device 100 into position and then may be removed prior to insertion of the expandable tool 180 within the device 100.

The first arm 184 of the portion 182 may include a top surface that engages third element 150. The second arm 186 may include a bottom surface that engages the first element 110, or the second element 130, or both elements 110, 130. The expandable device 180 further includes a member 181 having a distal end 181D coupled to the proximal end of the pair of member 187a via the pin $186_{P2}$. In operation, the member 181 may be moved distally, the member 181 slideably coupled to the second arm 86, causing the proximal end of the members 187a to move along the arm 186 toward the distal end of member 187b. In response to this movement, the proximal end of the member 187b moves along arm 184 toward the distal end of members 187a, resulting in the arm 184 moving away from arm 186, expanding the expandable tool 180.

The expanding device 180 may be utilized for assertively expanding and contracting the intervertebral device 100. For example, the device 180 may assertively expand the intervertebral device 100 through operation as described immediately above, and may assertively contract or collapse the intervertebral device 100 through methods opposite to those above. As depicted in FIG. 2D, portions of each arm 184, 186 may contact each corresponding element 150, 110, respectively, allowing for controlled movement in both an expanding direction and a collapsing direction.

Figure 3C:
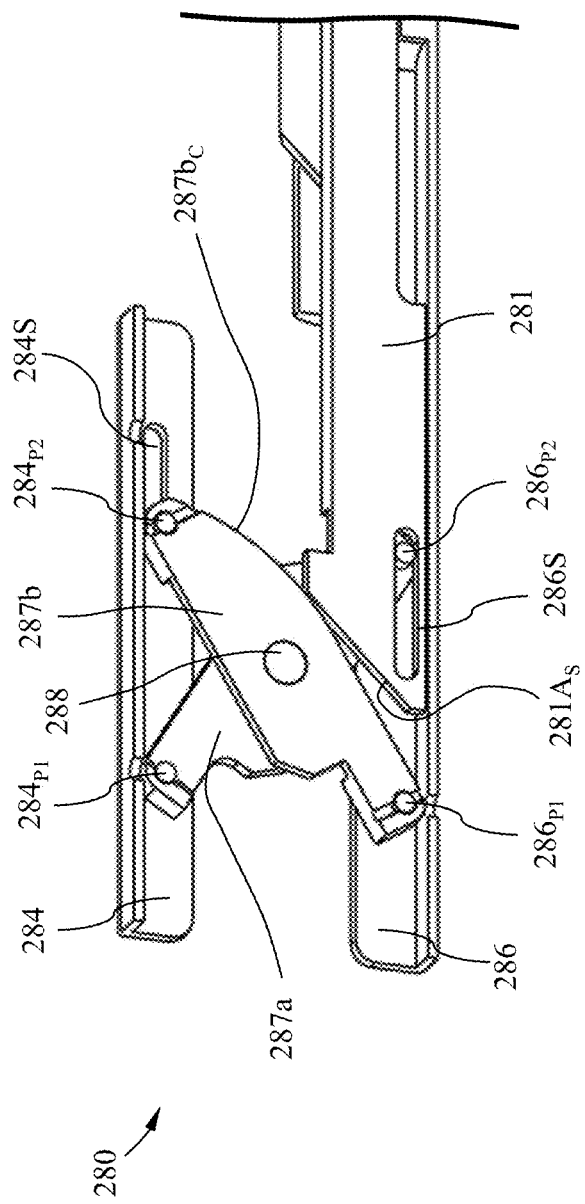
FIG. 3C is another partial section view of the exemplary delivery device of FIG. 3A.

Turning to FIGS. 3A-3C, a second delivery system 270 includes an expandable device 280, the expandable device depicted in cross-section in FIGS. 3B and 3C. As with delivery system 170, delivery system 270 includes a tubular member 272 that is configured to engage or otherwise couple to an intervertebral device, such as device 100 for example. Expandable device 280 includes an expandable distal portion 282. The expandable distal portion 282 includes a first arm 284, a second arm 286, a pair of members 287a and a member 287b. Members 287a and arm 287b are rotatably coupled through a hinge 288. A distal end of each of the members 287a is rotatably coupled to the arm 284 with a pin 284$_{P1}$ and a proximal end of each of the members 287a is slideably attached to arm 286 through the cooperation of a pin 286$_{P2}$ and corresponding slot 286S. Similarly, a distal end of the member 287b is rotatably coupled to the arm 286 with a pin 286$_{P1}$, and a proximal end of the member 287b is slideably coupled to the arm 284 through the cooperation of a pin 284$_{P2}$ and corresponding slot 284S. The distal end of the arm 286 may include a tab 286D (not shown), similar to tab 186D of expandable device 180 for example.

As with expandable device 180, the first arm 284 of the portion 282 may include a top surface that engages third element 150. The second arm 286 may include a bottom surface that engages the first element 110, or the second element 130, or both elements 110, 130. The expandable device 280 further includes a member 281 having a distal end 281D coupled to the proximal end of the pair of members 287a via the pin 286$_{P2}$. The proximal end of the arm 287b further includes a curved surface 287b$_C$ that is configured to engage the surface 281A$_S$. Accordingly, in operation, the member 281 may be moved distally, the member 281 slideably coupled to the second arm 286, the distal surface 281A$_S$ of the member 281 engaging the curved surface 287bC of the arm 287b, causing the proximal end of the member 287b to move vertically, resulting in the arm 284 moving away from arm 286, expanding the expandable tool 280. As should be readily understood, the characteristics of the curved surface 287b$_C$ define the rate of expansion, e.g., the rate at which the arm 284 moves away from arm 286. The angled surface 281A$_S$, also cooperates with the curved surface 287b$_C$ to further define the rate of expansion. While shown as forming an angle with respect to a longitudinal axis of the member 281, the angled surface 281A$_S$ may include a curve, or may include a combination of linear and curved portions.

As with the expanding device 180, the expanding device 280 may be utilized for assertively expanding and contracting the intervertebral device 100. For example, the device 280 may assertively expand the intervertebral device 100 through operation as described immediately above, and may assertively contract or collapse the intervertebral device 100 through methods opposite to those above.

Figure 4A:
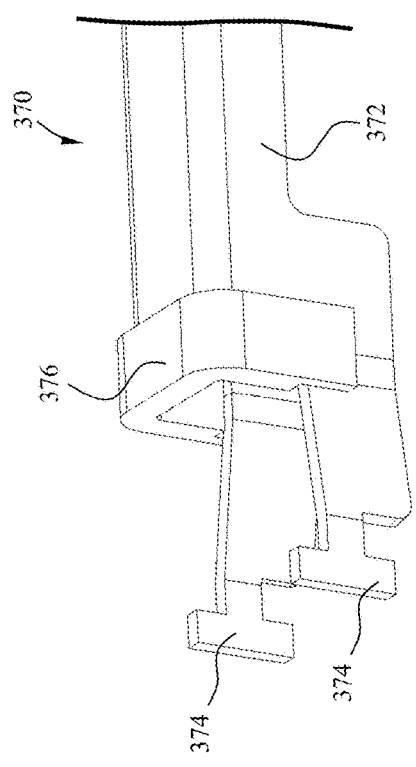
FIG. 4A is perspective view of a portion of another exemplary delivery device.
Figure 4B:
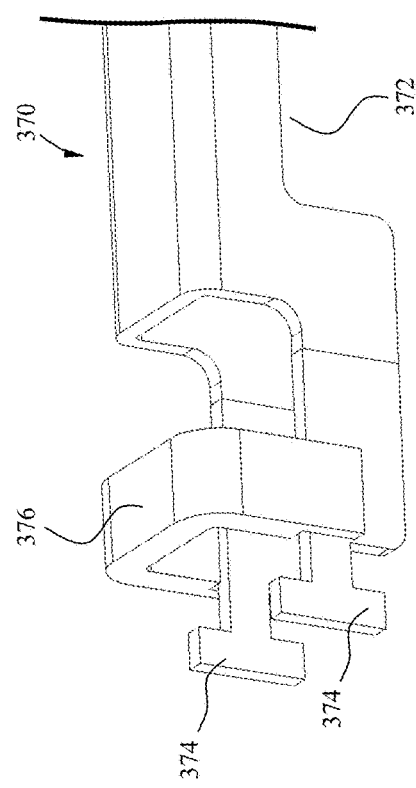
FIG. 4B is a perspective view of the portion of the exemplary delivery device of FIG. 4A.

Turning to FIG. 4A, another exemplary insertion tool 370 includes an outer member 372 formed in a U-shape along its longitudinal axis, ending in a pair of arms 374 having distal ends of particular geometric shapes, and a tab 376 adapted to slide along the arms 374. The tab 376 has an inner dimension distance which is equal to a minimal inner dimension distance between the arms 374, the arms being further adapted to have a maximum inner dimension distance at its distal tip, as generally depicted in FIG. 4A. With reference also to FIG. 4B, in operation, the tab 376 is advanced along the arms 374 to decrease the inner dimension distance to that of the tab 376, the tab 376 being adapted to maintain its shape in light of any forces present as a result of contact with the arms 374.

Turning also to FIG. 4C, the exemplary insertion tool 370 and a second member 230 of another intervertebral device 200 are depicted, intervertebral device 200 being similar to intervertebral device 100 except as noted below. The second member 230 is similar to second member 130 of intervertebral device 100 except that the second member 350 includes a recess 238 in an inner wall of the second member 230, the recess 238 including a portion that geometrically matches the geometric shape of at least a portion of the distal end of arms 374. An output dimension distance of the arms 374 may be equal to or less than an inner dimension distance of the second member 230 such that the distal end of the arms 374 may be inserted into the second member 230, as generally depicted in FIG. 4C. Turning also to FIG. 4D, the tab 376 can then be moved in a proximal direction resulting in the distal tip of arms 374 to expand with respect to each other and engage the recesses 238 of second element 230. Once the arms 374 were positioned within the recesses 238, advancing or retracting the insertion tool 370 results in correspondingly advancing or retracting the second element 230. Accordingly, once the intervertebral device 200 is expanded to a desired height, the insertion tool 370 may be moved distally to correspondingly distally move the second element 230 or device 100. As discussed above, the engaging members of the second element 230 and the third member 250 would engage and maintain the position of the third element 250 with respect to the first element 110. Alternatively, if it is desired to collapse the intervertebral device 200, with the device 200 in the expanded locked position, a portion of the insertion device 370 may then be moved proximally resulting in a corresponding proximal movement of the second element 230. Simultaneously, the expanding tool 180 may be holding the current position of the third element 250 with respect to the first element 210, or if applicable, and/or the second element 230. The intervertebral device 200 may then be collapsed with the expanding tool 180 to a desired height. Once the desired height is reached, once again the second element 230 can be moved distally such that the engaging members of the second element 230 and the third element 250 engage to maintain the position of the third element 250 with respect to the first element 210.

Turning to FIGS. 5A-5D, another exemplary insertion tool 470 is adapted to engage a second element 330 of another exemplary intervertebral device 300, intervertebral device 300 being similar to intervertebral device 100 except as noted below. The insertion tool 470 includes an elongated body portion 472 ending in a pair of arms 474, each having a geometric shape. The geometric shape of the arms 474 of insertion tool 470 is different when compared to the geometric shape of the arms 374 of insertion tool 370. The arms 474 are adapted to engage corresponding geometric shapes 332 of the second element 330 of device 300. Moving the insertion tool 470 toward the second element 330 results in the deflection of tips 474 above the geometric shapes 332 of the second element 330, as best viewed in FIG. 5B. The arms 474 may rotate as a result of contact with the second element 330, or may be rotated through use of a control (not shown). Accordingly, the arms 474 may be controllably extended or rotated to move the distal arms 474 vertically up and down, for example.

Figure 5A:
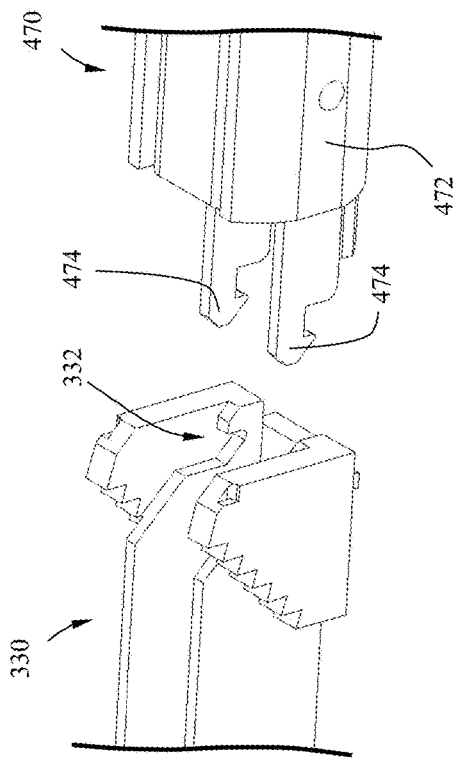
FIG. 5A is a perspective view of a portion of another exemplary delivery device and a portion of another exemplary intervertebral device.
Figure 5B:
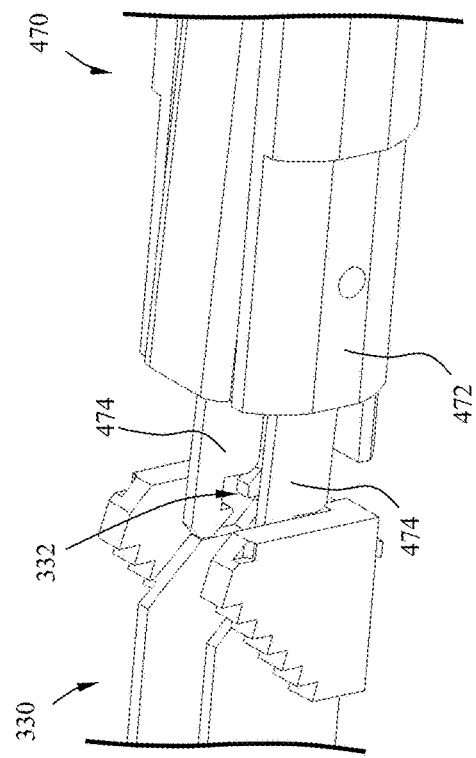
FIG. 5B is another perspective view of the portion of the exemplary delivery device of FIG. 5A and the portion of the exemplary intervertebral device of FIG. 5A.
Figure 5C:
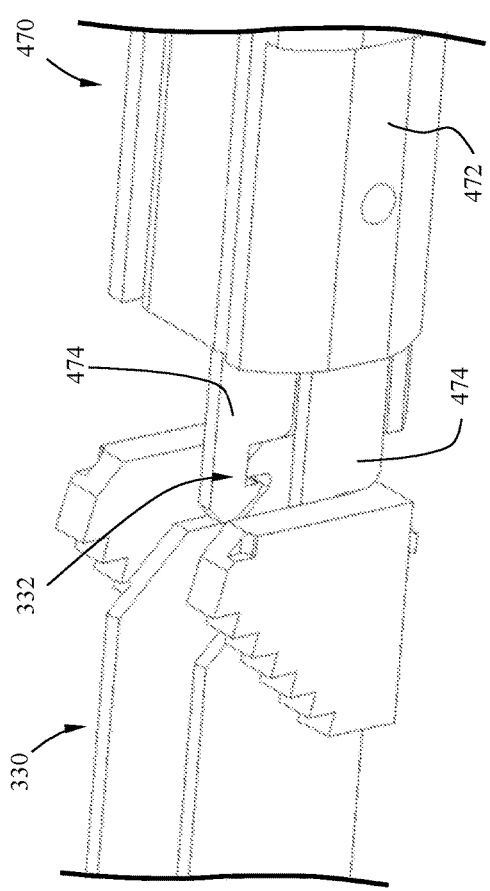
FIG. 5C is still another perspective view of the portion of the exemplary delivery device of FIG. 5A and the portion of the exemplary intervertebral device of FIG. 5A.
Figure 5D:
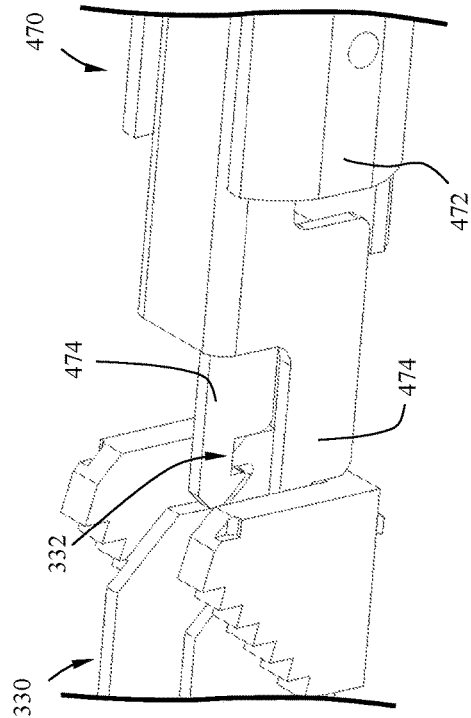
FIG. 5D is yet another view of the portion of the exemplary delivery device of FIG. 5A and the portion of the exemplary intervertebral device of FIG. 5A.

Once the arms 474 have engaged the geometric structure 332 of the second element 330, as best shown in FIG. 5C, the elongate member 472 may be moved distally or proximately to correspondingly move the second element 330 to engage or release from the third element 350. As described above, as the second element 330 engages the third element 350, the position of the third element 350 is maintained with respect to the first element 310, and as the second element 330 is released from the third element 350, the position of the third element 350 with respect to the first element 310 may be expanded or collapsed, as desired. As shown in FIG. 5D, the elongated member 472 may be extended to lock the position of the third element 350 with respect to the first element 110 and/or the second element 330.

Figure 6A:
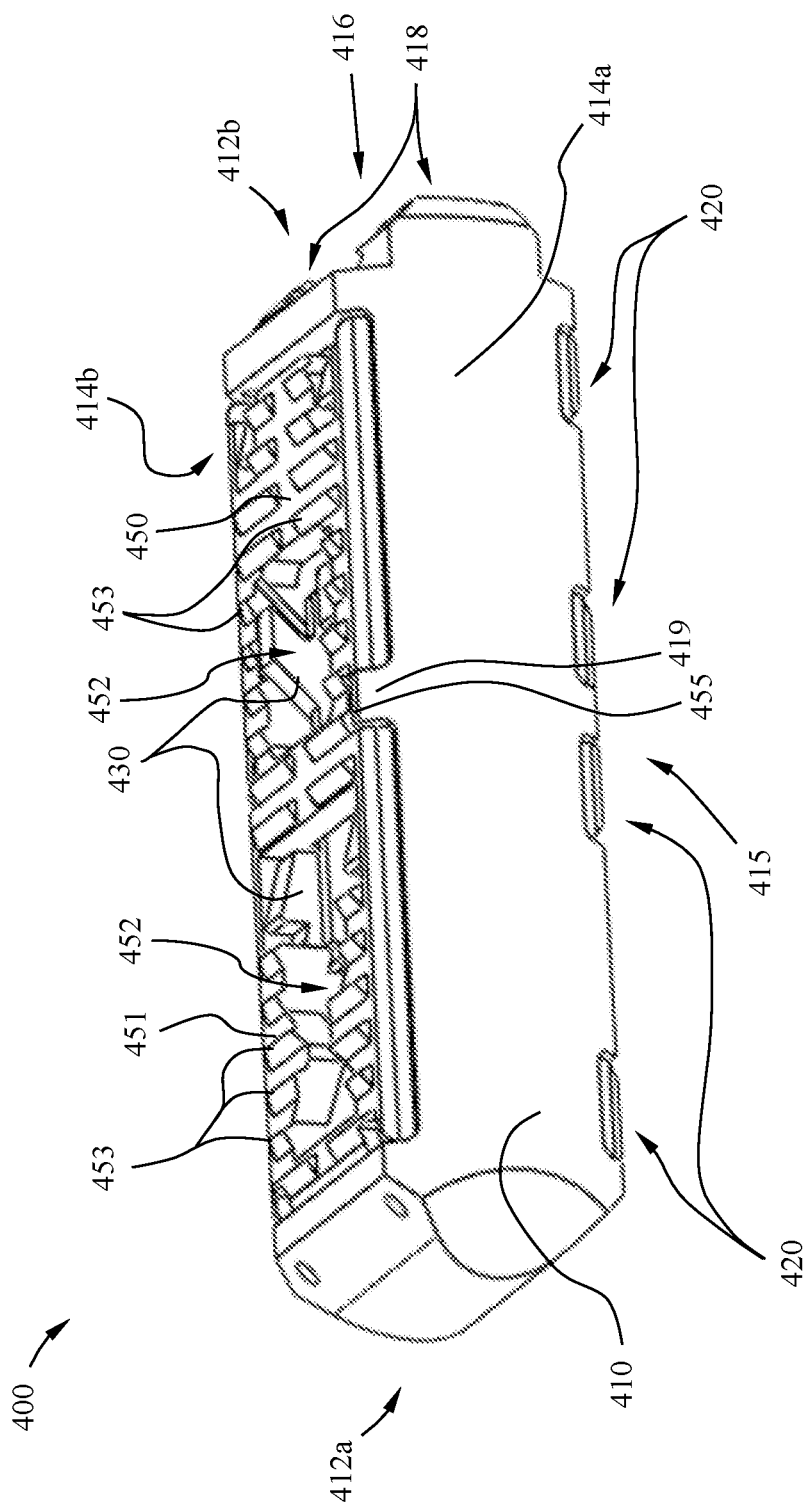
FIG. 6A is a perspective view of another exemplary delivery device.
Figure 6B:
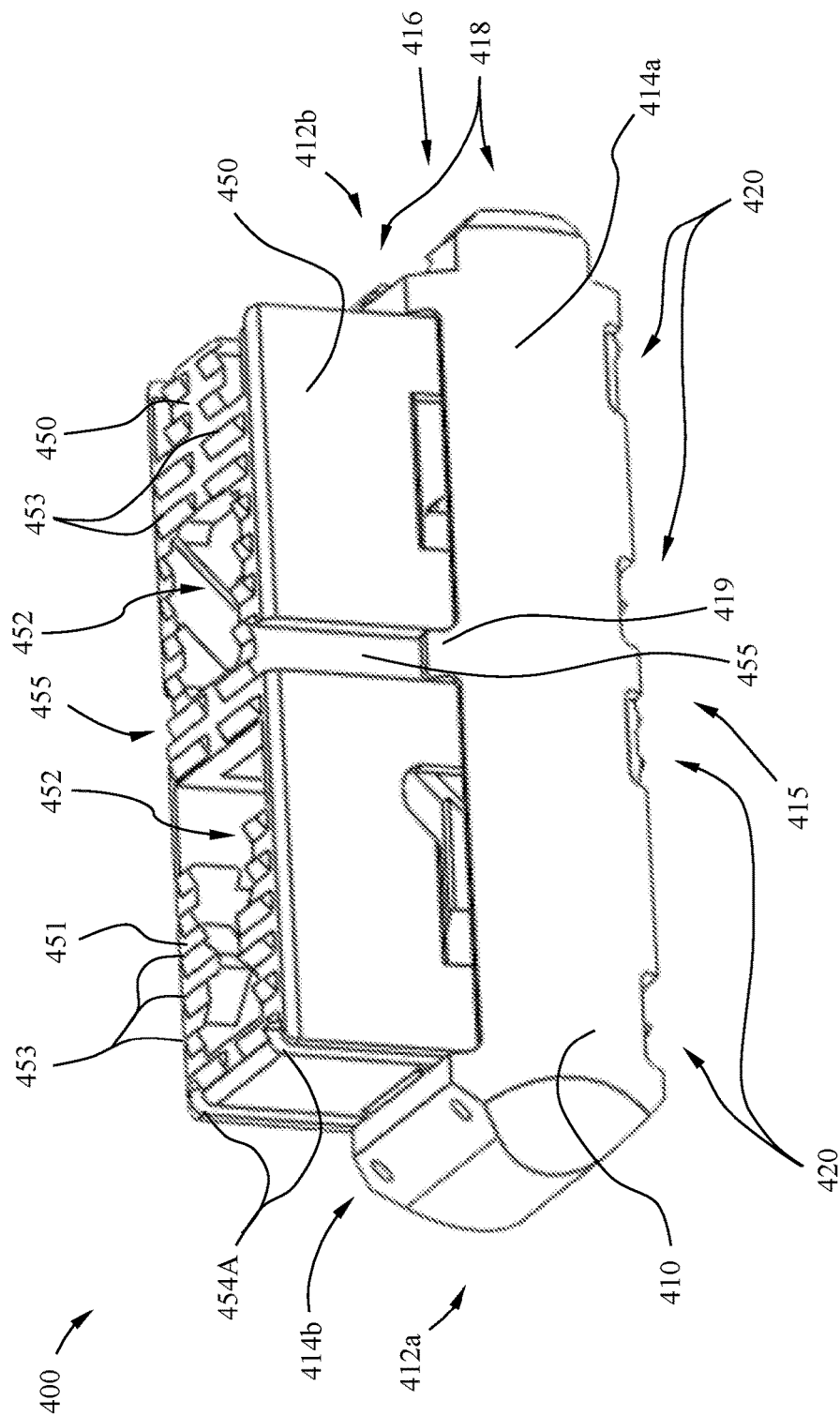
FIG. 6B is a perspective view of the exemplary delivery device of FIG. 6A in a second configuration.

Turning to FIGS. 6A and 6B, a perspective view of another exemplary intervertebral device 400 includes a first element 410, a second element 430, and a third element 450.

As will be better understood in the discussion below, the elements 410, 430, 450 cooperate such that the intervertebral device 400 geometric height may have a minimum, collapsed configuration, as depicted in FIG. 6A, and a maximum, expanded configuration, as depicted in FIG. 6B and discussed in greater detail below. The first element 410 may also be referred to as a base 410, the second element 430 may also be referred to as a first body portion 430, and the third element 450 may also be referred to as a second body portion 450.

The first element 410 is configured to provide a base or outer structure for the intervertebral device 400, and includes two ends or end portions 412a, 412b and two sides or side portions 414a, 414b. A bottom portion 415 includes one or more openings 420, as other elements 430, 450 may do as well, to allow for therapeutic agents, including bone growth enhancing materials, to pass therethrough. One end, e.g. end 412b, may include an opening 416 for passing delivery tools utilized for expanding, contracting, or locking the intervertebral device 400. The end 412b may also include threaded structures 418, which allow for attachment to a delivery tool or system (not shown), as described below with respect to FIG. 7.

The third element 450 is slidably interfaced to the first element 410 such that the third element 450 at least slides vertically with respect to the first element 410. The third element 450 may include one or more openings 452 to allow for passage or introduction of therapeutic elements or agents, including bone growth enhancing materials, therethrough. The third element 450 may also include recessed surfaces 455 adapted to receive a portion 419 of the first element 410 to limit the movement of the third element 450 to substantially one direction with respect to the first element 410. As with intervertebral device 100, each of the sides or sidewalls 414a, 414b of the first element 410 may be curved along its height to correspond to a delivery tube or cannula (not shown), as part of a delivery system. The sidewalls 414a, 414b may have other geometric cross-sections to correspond to elements of alternative delivery systems. The second element 430 may be positioned at least partially within the third element 450. A top surface 451 of third element 450 may include one or more protrusions 453 adapted or configured to engage a biological tissue surface, such as a vertebral surface.

Turning to FIG. 6B, the exemplary intervertebral device 400 is depicted in an expanded configuration. As discussed above, protrusions 419 of the first element 410 may cooperate with recesses 454, as well as other side walls of first element 410 cooperating with side walls of the third element 450, to maintain the movement of the third element 450 in a substantially single direction with respect to the first element 410. The second element 430 may then be positioned to lock the position of the third element 450 with respect to the first element 410, at a desired intervertebral device 400 height, for deployment between two adjacent vertebrae for example. As shown in FIG. 6B, third element 450 may include additional recesses 454A configured to slideably couple to corresponding protrusions of the first element 410 (not shown) to provide additional stability, if desired.

Figure 6C:
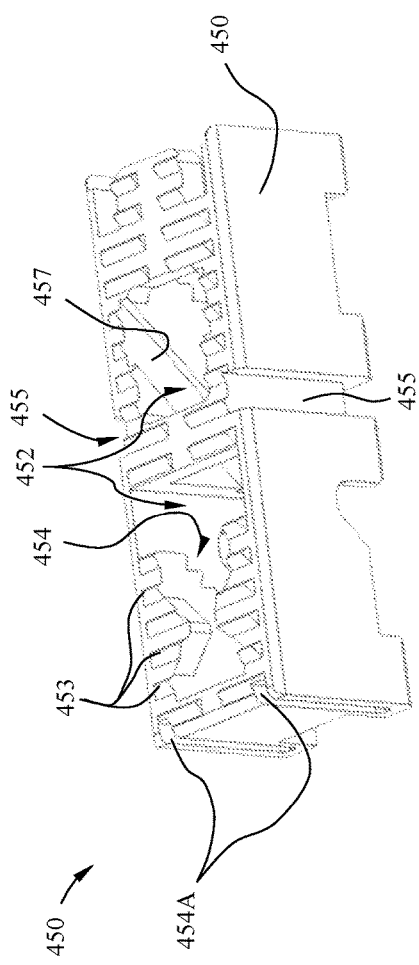
FIG. 6C is a perspective view of an element of the exemplary delivery device of FIG. 6A.
Figure 6D:
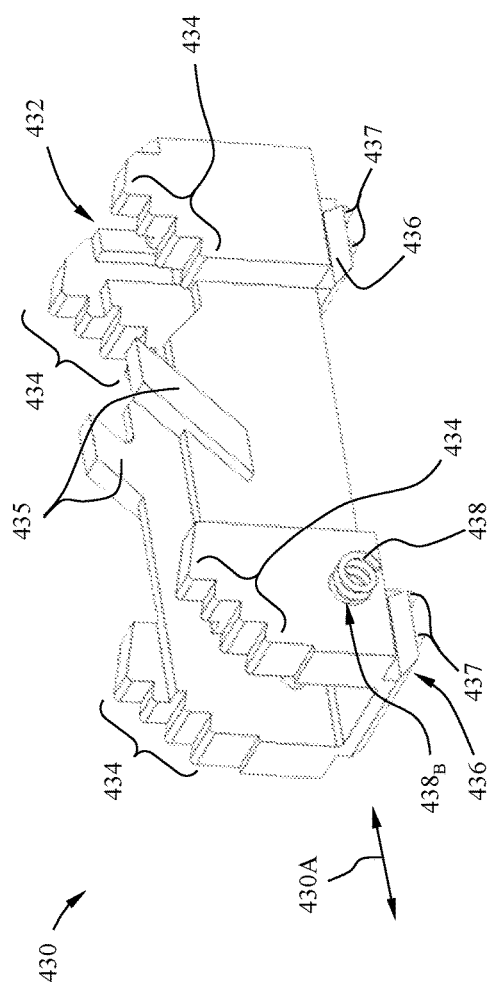
FIG. 6D is a perspective view of another element of the exemplary delivery device of FIG. 6A.
Figure 6E:
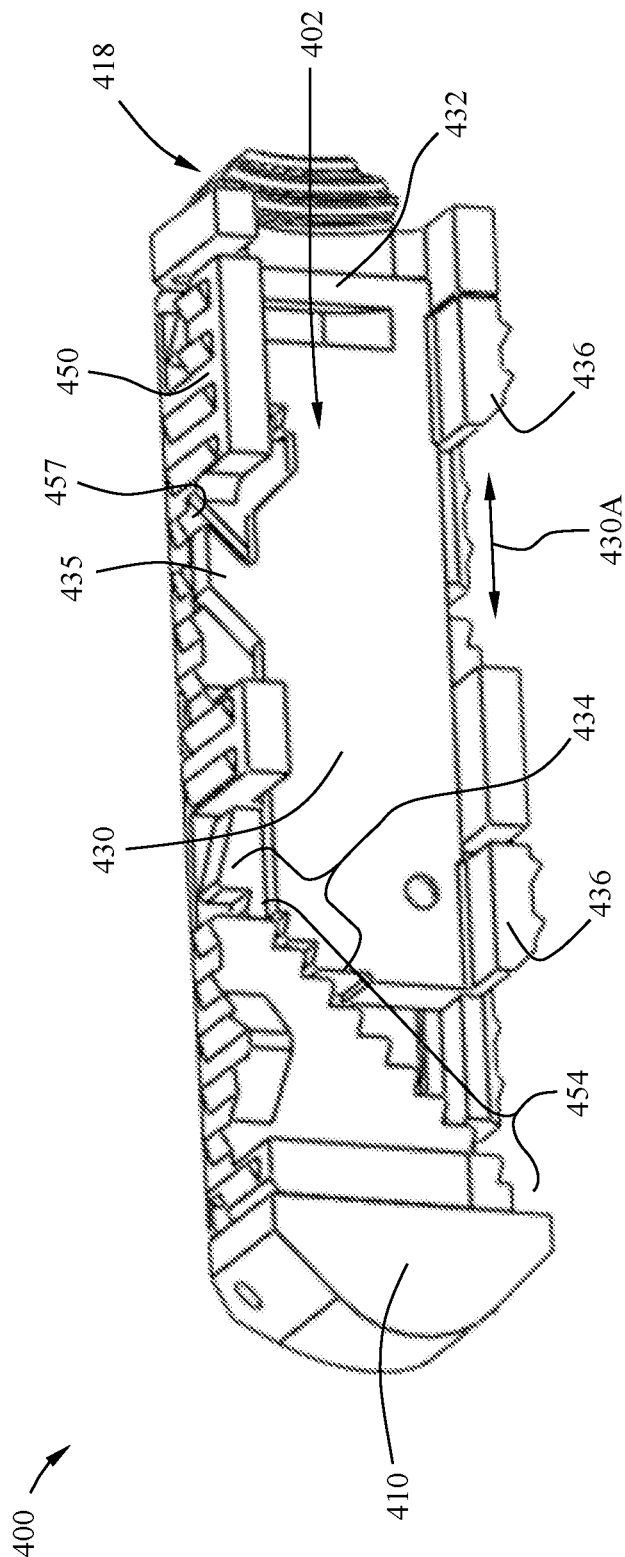
FIG. 6E is a partial section view of the exemplary delivery device of FIG. 6A.

Turning now to FIGS. 6C-6E, additional details of the first, second, and third element 410, 430, 450 are described. More specifically, FIG. 6C depicts third element 450, FIG. 6D depicts second element 430, and FIG. 6E depicts intervertebral device 400 in cross-section. The second element 430 may also include a geometric structure 432 adapted to interface to a tool (not shown) that moves the second element 430 in the directions indicated by an arrow 430A, as part of an insertion or delivery tool for example.

The third element 450 may include a number of engaging elements 454 which are adapted to engage corresponding engaging elements 434 of the second element 430. Also, the second element 430 may include cross members 436 which may be adapted to slide upon tissue, for example bone tissue. Cross members 436 may include one or more protrusions 437 to better engage a tissue surface once, the intervertebral device is deployed. While depicted as engaging teeth, the engaging members 434, 454 may take on any suitable geometric configuration that allows for maintaining the position of the third member 450 with respect to the first member 410. For example, the engaging members 454 may be semicircular recesses and the engaging member 434 may be corresponding semicircular tabs adapted to engage the semicircular recesses.

The second element 430 may also include protrusions 435 configured to be slideably received in respective recessed areas 457 of third element 450. The various surfaces of the protrusions 435 and recessed areas 457 may act to further encourage collapse of the intervertebral device 400 that is initially expanded, for example, to the expanded configuration of FIG. 6B. Accordingly, the recessed areas 457 must be sized to allow for expansion of the intervertebral device 400, as described in greater detail below with respect to FIG. 7, with or without forced movement of the second element 430. The second element 430 may also include a spring 438, provided in an associated bore $438_B$, to help assist in maintaining the second element 430 with other elements 410, 450.

Figure 7C:
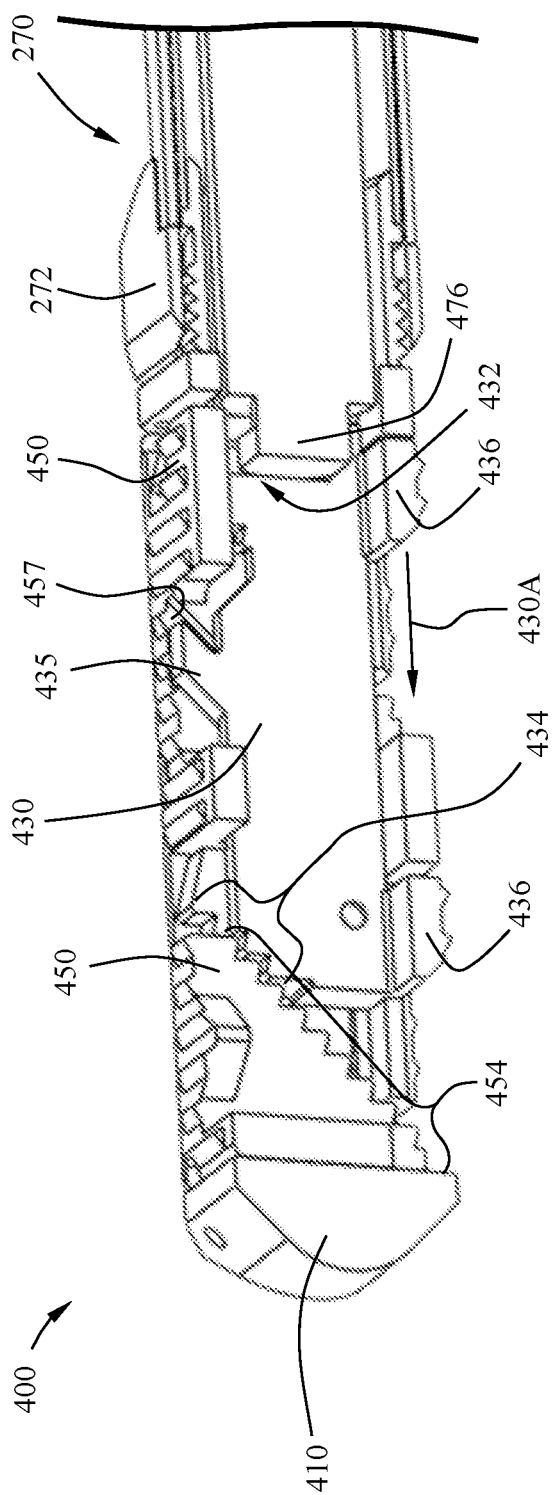
FIG. 7C is a perspective view of a portion of another exemplary delivery device and the portion of the exemplary intervertebral device of FIG. 6A.

In operation, with reference also to FIGS. 7A and 7B, which depict the intervertebral device 400 in cross-section, an expanding tool, such as expanding tool 270 for example, may be positioned within an internal space 102 of the intervertebral device 100, as described in great detail above with respect to delivery tool 170, which is similar to delivery tool 270, in FIG. 2. The expanding tool 270 may be configured to engage both the first element 410 and the third element 450 such that when the expanding tool is expanded the third element 450 moves substantially vertical with respect to the first element 410, as generally indicated by arrow 450A. Once the device 400 has been expanded, the expanding tool 270, or another tool (not shown), may be utilized to then translate or move the second element 430 in the direction of arrow 430A, as desired, the engaging members 454, 434 engaged to maintain the position of the third element 450 with respect to the first element 410 and/or the second element 430. For example, with reference to FIG. 7C, which depicts the delivery tool with the expandable device 180 removed for illustration purposes only, the delivery tool 270 may include a member 476. Member 476 may include a distal end 476D configured to couple with geometric structure 432 such that movement of the member 476 in one or more directions as indicated by arrow 430A results in corresponding movement of the second element 430. Accordingly, the expanding device 180 may first be operated to expand the intervertebral device 400, then the member 476 may be operated to distally move the second element 430 such that the engaging elements 454, 434 are coupled or engaged, locking the intervertebral device 400 such that the third element 450 is held in fixed relation with respect to the first element 410 and/or the second element 430. The intervertebral device 400 may be collapsed a certain height by expanding the expanding device 280 until the arms 284, 286 contact the elements 450, 410, respectively. The member 476 may then be utilized to move the second member 430 in a proximal direction, allowing the expanding device 180 to collapse the intervertebral device 400 such that the height is reduced. Once at a desired new height, the member 476 may then be utilized to lock the intervertebral device 400 in the current position.

Turning to FIGS. 8A-8D, another exemplary intervertebral device 500 includes a first element 510, a second element 530 and a third element 550. The second element 530 is configured to move generally along a longitudinal axis of the first element 510, while the third element 550 is configured to move in a vertical direction with respect to a longitudinal axis of the first element 510 and also in direction along a longitudinal axis of the first element 510 when the intervertebral device 500 is in a locked position or configuration. The first element 510 includes a drive mechanism 524. The drive mechanism 524 including a drive member 526 slideably coupled to first element 510 at an opening 523, and adjustably coupled to the second element 530, in similar fashion as discussed below in FIG. 9C with respect to intervertebral device 600. The drive mechanism 524 is configured to adjustably move the second element 530 distally and proximally with respect to a longitudinal axis of the first element 510. As will become apparent with respect to the discussion below, as the second element 530 is moved to a distal end of the first element, the intervertebral device 500 is locked, preventing further movement of the elements 510, 530, 550 with respect to each other.

The third element 550 may include engaging members 554, each including one or more pins $554_P$. The inner wall of the first element 510 may include one or more slots 512 having curved portions or engaging elements 514 configured to accept a portion of the one or more pins $554_P$. An expandable tool (not shown) may be positioned within a space or void 556 and expanded causing the device 500 to expand, the pins $554_P$ moving in a direction depicted by arrow $V_A$ for example. For illustration purposes only, device 500 is depicted in an expanded configuration in FIG. 8D, the first element 510 removed. Once a desired expansion is achieved the drive mechanism 524 is operated to rotate the drive member 526 in a first direction as depicted by arrow $H_A$ relative to the first element 510. Accordingly, movement of the second element 530 results in corresponding movement of the third element 550 in the same direction, the pins $554_P$ engaging respective curved portions 514 of slots 512 maintaining the position of the third element 550 with respect to the first element 510. Operating the drive mechanism 524 in a second opposite direction allows the pins $554_P$ to disengage the curved portions 514 of slots 512 and allowing the expansion tool to collapse the device 500, as desired.

Figure 9C:
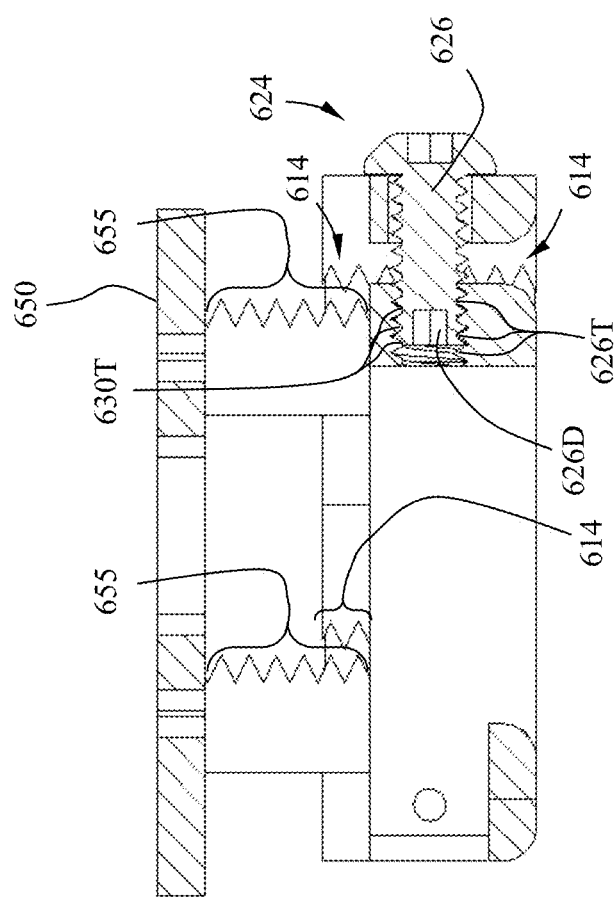
FIG. 9C is a perspective view of another portion of the exemplary intervertebral device of FIG. 9A.

Now turning to FIGS. 9A-9C, an alternative embodiment 600 is depicted including a first element 610, a second element 630, a third element 650 and a drive mechanism 624 coupled to the first element 610 and the second element 630. The third element 650 includes engaging members 654 having engaging surfaces 655, while the first element 610 may be configured to include mating engaging surfaces 614. As with the embodiment 500, the second element 630 and third element 650 are slideably coupled to the first element 510. The drive mechanism 624 includes a drive member 626 having threads 626T which couple with threads 630T of the second element 630 such that rotation of the driver 626 results in movement of the second element 630 along a longitudinal axis of the first element 610.

In operation, a delivery tool (not shown) may be utilized to expand the intervertebral device 600, expansion tool 180 for example. Once a desired height of the intervertebral device 600 is achieved, the drive member 626 may then be operated with an elongate member (not shown) as part of the delivery tool for example, having a driver tool configured to interface with drive socket 626D. For example, rotation of the drive member 626 in a first direction results in the movement of the second element 630 in a direction depicted by arrow $H_A$, a direction substantially parallel to a longitudinal axis of the first element 510, until the mating surfaces 655, 614 engage and hold the third element 650 relative to the first element 610. Operation of the drive mechanism 624 in a second direction results in disengagement of the mating surfaces 655, 614 allowing for the collapse of device 600, if desired.

The expandable intervertebral devices described herein may be made from any suitable biocompatible material, including but not limited to metals, metal alloys (e.g. stainless steel) and polymers (e.g. polycarbonate), and may be formed using any appropriate process, such as screw-machining or molding (e.g. injection molding). The intervertebral devices herein may be sized for minimally invasive procedures having operating lumens at about 12 mm or less.

What is claimed is:

1. An intervertebral device, comprising:
a base having a bottom surface, a first end, a second end, and a longitudinal axis extending from the first end to the second end;
a first body portion slidably coupled to the base and configured to move in a first direction with respect to the base, the first body portion including a bottom surface and a first engaging element; and
a second body portion slidably coupled to the base and configured to move in a second direction with respect to the base, the second body portion including a top surface and a second engaging element,
the first engaging element of the first body portion being configured to couple to the second engaging element of the second body portion, such that coupling of the first and second engaging elements prevents movement of the second body portion in a third direction with respect to the base when a compression force is present between the top surface of the second body portion and the bottom surface of the base, the third direction being substantially opposite to the second direction,
the first and second body portions being configured such that movement of the first body portion in the first direction does not result in movement of the second body portion in the second direction,
the first body portion configured to be positioned at one of a plurality of positions along the longitudinal axis of the base, the second body portion configured to be positioned at one of a plurality of positions at least perpendicular to the longitudinal axis of the base, each of the plurality of positions of the first body portion corresponding to a respective one of the plurality of positions of the second body portion.

2. The device of claim 1, wherein the base, the first body portion, and the second body portion are configured to define a void central to the device.

3. The device of claim 1, wherein the first direction is substantially parallel to the longitudinal axis of the base.

4. The device of claim 1, wherein the second direction is substantially perpendicular to the longitudinal axis of the base.

5. The device of claim 1, wherein the first direction and the second direction are substantially perpendicular to each other.

6. The device of claim 1, wherein the top surface of the second body portion is configured to interface with a first biological tissue, and the bottom surface of the base is configured to interface with a second biological tissue.

7. The device of claim 1, wherein the first body portion includes a surface configured to interface with biological tissue.

8. The device of claim 1, wherein each of the first and second engaging elements have geometric shapes, a portion of the geometric shape of the first engaging element configured to couple to a portion of the geometric shape of the second engaging element.

9. The device of claim 8, wherein the geometric shape of each of the first and second engaging elements includes a shape selected from a group consisting of a triangle, a circle, a rectangle, and a cylinder.

10. The device of claim 8, wherein the geometric shape of each of the first and second engaging elements includes a tooth structure.

11. The device of claim 8, wherein the geometric shape of each of the first and second engaging elements is a curvilinear geometric shape.

12. The device of claim 1, wherein the first engaging element is one of a plurality of first engaging elements, and the second engaging element is one of a plurality of second engaging elements.

13. The device of claim 12, wherein the first engaging element engages a first of the plurality of second engaging elements corresponding to a first height of the intervertebral device, and the first engaging element engages a second of the plurality of the second engaging elements corresponding to a second height of the intervertebral device.

14. The device of claim 1, wherein the first direction is in a direction toward a distal end of the device along a longitudinal axis of the base.

15. The device of claim 1, wherein the first direction is in a direction toward a proximal end of the device along a longitudinal axis of the base.

16. The device of claim 1, wherein each of the plurality of positions of the first body portion corresponds to a respective one of a plurality of heights of the device.

* * * * *